(12) United States Patent
Livingston

(10) Patent No.: US 8,754,045 B2
(45) Date of Patent: Jun. 17, 2014

(54) ENZYMATIC DEBRIDEMENT THERAPY FOR ABNORMAL CELL PROLIFERATION

(76) Inventor: James A. Livingston, Macon, GA (US)

( * ) Notice: Subject to any disclaimer, the term of this patent is extended or adjusted under 35 U.S.C. 154(b) by 872 days.

(21) Appl. No.: 11/803,304

(22) Filed: May 14, 2007

(65) Prior Publication Data

US 2008/0044459 A1 Feb. 21, 2008

Related U.S. Application Data

(60) Provisional application No. 60/799,766, filed on May 12, 2006.

(51) Int. Cl.
*A61K 38/48* (2006.01)
*A61K 38/43* (2006.01)

(52) U.S. Cl.
CPC ........... *A61K 38/482* (2013.01); *A61K 38/4826* (2013.01); *A61K 38/4873* (2013.01); *A61K 38/488* (2013.01); *A61K 38/4886* (2013.01)
USPC ....... 514/19.3; 514/19.4; 514/19.5; 514/19.6; 424/94.1; 424/94.64

(58) Field of Classification Search
CPC ..... A61K 38/43; A61K 38/48; A61K 38/482; A61K 38/4826; A61K 38/4873; A61K 38/488; A61K 38/4886
USPC ............. 514/19.3, 19.4, 19.5, 19.6; 424/94.1, 424/94.64
See application file for complete search history.

(56) References Cited

U.S. PATENT DOCUMENTS

| | | | |
|---|---|---|---|
| 4,522,811 A | 6/1985 | Eppstein | |
| 5,595,756 A * | 1/1997 | Bally et al. | 424/450 |
| 5,651,986 A | 7/1997 | Brem | |
| 5,902,600 A | 5/1999 | Woller | |
| 6,399,092 B1 | 6/2002 | Hobson | |
| 6,548,556 B2 | 4/2003 | Hobson | |
| 6,811,788 B2 | 11/2004 | Yu | |
| 7,217,739 B2 | 5/2007 | Wondrak | |
| 2002/0044919 A1 * | 4/2002 | Yu | 424/85.1 |
| 2003/0026794 A1 | 2/2003 | Fein | |
| 2003/0198631 A1 | 10/2003 | Shi | |
| 2003/0198632 A1 | 10/2003 | Shi | |

FOREIGN PATENT DOCUMENTS

WO WO 2005/018695 3/2005

OTHER PUBLICATIONS

Definition of derivative from http://cancerweb.ncl.ac.uk/omd/about.html, pp. 1-5. Accessed Jul. 7, 2005.*
Sporn MB, Suh N, "Chemoprevention of cancer," Carcinogenesis, 2000, 21(3): 525-530.*
Auerbach R, Akhtar N, Lewis RL, Shinners, BL, "Angiogenesis assays: Problems and pitfalls," Cancer and Metastais Reviews, 2000, 19: 167-172.*
Gura T, "Systems for Identifying New Drugs Are Often Faulty," Science, 1997, 278: 1041-1042.*
Jain RK, "Barriers to Drug Delivery in Solid Tumors," Scientific American, 1994, 58-65.*
Cancer Drug Design and Discovery Neidle, Stephen, ed. (Elsevier/Academic Press, 2008) pp. 427-431.*
Alley, M. C., et al., "Feasibility of Drug Screening with Panels of Human Tumor Cell Lines Using a Microculture Tetrazolium Assay." Cancer Research. 48:589-601 (1988).
Bale S. "A Guide to Wound Debridement." Journal of Wound Care. 6:179-182 (Apr. 1997).
Boyd, M. R., and Paull, K. D., "Some Practical Considerations and Applications of the National Cancer Institute In Vitro Anticancer Drug Discovery Screen." Drug Development Research. 34:91-109 (1995).
Grever, M. R., et al., "The National Cancer Institute: Cancer Drug Discovery and Development Program." Seminars in Oncology. 19(6):622-638 (1992).
Horobin et al., "Promotion of Human Dermal Fibroblast Migration, Matrix Remodelling and Modification of Fibroblast Morphology within a Novel 3D Model by *Lucilia sericata* Larval Secretions." J Invest Dermatol. 126(6):1410-8 (Jun. 2006).
Reames M K, et al. "The Use of Maggots in Wound Debridement." Annals of Plastic Surgery. 21:388 (1988).
Sherman, R A, Wyle, F, Vulpe, M: "Maggot Debridement Therapy for Treating Pressure Ulcers in Spinal Cord Injury Patients." Journal of Spinal Cord Medicine. 18(2): 71-74 (1995).
Sieggreen M Y and Maklebust J. "Debridement: Choices and Challenges." Advances in Wound Care. 10: 32-37 (Mar./Apr. 1997).

* cited by examiner

*Primary Examiner* — Julie Ha
(74) *Attorney, Agent, or Firm* — King & Spalding

(57) ABSTRACT

Compositions and methods are provided to destroy internal cancerous lesions selectively by the administration of a combination of a debridement protease enzyme and a denaturant of cell structural proteins and or cell adhesion proteins.

16 Claims, 9 Drawing Sheets

ENZYMATIC DEBRIDEMENT THERAPY FOR ABNORMAL CELL PROLIFERATION

CROSS-REFERENCE TO RELATED APPLICATIONS

This application claims priority to U.S. Provisional Application No. 60/799,766, filed May 12, 2006.

FIELD OF THE INVENTION

This invention provides compositions and methods for the treatment of disorders characterized by abnormal cell proliferation, such as neoplasms.

BACKGROUND OF THE INVENTION

Debridement is the process of removing non-living tissue from wounds, burns and ulcers. The non-living tissue retards healing and can lead to inflammation and infection when dead tissue becomes colonized by bacteria. Sieggreen M Y and Maklebust J. "Debridement: Choices and Challenges." *Advances in Wound Care*, 10 (March/April 1997): 32-37; Bale S. "A Guide to Wound Debridement." *Journal of Wound Care* 6 (April 1997): 179-182. The goal of debridement therapy is to remove the non-living tissue so that the remaining tissue can begin to heal. A variety of debridement methods are known, including sharp, mechanical, biological, autolytic and enzymatic debridement.

Sharp debridement, also known as surgical debridement, utilizes a sharp object such as a scalpel, scissors, or other instrument to cut dead tissue from a wound. Sharp debridement is fast and relatively selective, i.e., it causes limited damage to healthy or healing tissue. Depending on the location of the tissue to be removed, sharp debridement can be performed at a patient's bedside or in an operating room. Typically, sharp debridement is used to treat wounds that have a large amounts of necrotic material. Sharp debridement can be costly and painful.

Mechanical debridement involves repetitive application and removal of wound dressings. According to this method, a moistened dressing is allowed to dry overnight and adhere to the dead tissue. When the dressing is removed, the dead tissue is also removed. Mechanical debridement is time-consuming, often painful, and relatively un-selective, i.e., it can produce significant damage to healthy or healing tissue. It is typically suited to treatment of wounds that have a moderate amounts of necrotic material.

Biological debridement refers to the use of sanitary maggots under dressings to cleanse wounds. See Reames M K, et al. "The use of maggots in wound debridement." *Annals of Plastic Surgery.* 21: 388, 1988; Sherman, R A, Wyle, F, Vulpe, M: Maggot Debridement Therapy for treating pressure ulcers in spinal cord injury patients. *Journal of Spinal Cord Medicine*, 18(2): 71-74. 1995. This somewhat archaic procedure is the subject of renewed interest in recent years given its selectivity and high efficiency.

Autolytic debridement refers to the process by which dead and non-viable tissue is removed by the patient's own wound fluid, which contains growth factors, enzymes and immune cells (e.g., phagocytes) that can promote wound healing. This method utilizes occlusive or semi-occlusive dressings which maintain wound fluid in contact with the necrotic tissue. Autolytic debridement is very selective and relatively painless, but is also very slow.

Enzymatic debridement involves the use of enzymes from outside the body to remove non-living tissue. Debridement enzymes cut ("cleave" or digest) large immobile structural molecules of the cell into smaller molecules that can dissolve and migrate away. Most debridement enzymes cleave proteins, i.e., they are proteases. Enzymatic debriding agents are typically used in conjunction with moist dressings and autolytic debridement. Enzymatic debridement is relative fast and, in many cases, leaves no scar tissue.

Uses for debridement enzymes are discussed in Hobson et al., U.S. Pat. No. 6,548,556; Hobson et al., U.S. Pat. No. 6,399,092; and Jones et al., PCT Publication No. WO 2005/018695.

The effectiveness of enzymatic debridement varies with the type of enzyme used. Enzymes lie along a spectrum of selectiveness, which ranges from nonspecific (i.e., indiscriminate) digestion of protein substrates to extremely specific enzymes that can digest only one narrow type of target protein. Enzymes also differ in their productivity; the characteristic rate of digestion by an enzyme is expressed in units of activity (per gram of product), and the activity unit values are usually defined by international or pharmacopeial convention; a USP unit is defined in the United States Pharmacopeia. Many reagents and conditions can reduce the effectiveness of cleavage by a given enzyme.

Most debridement enzymes in common use are derived from non-human sources, including animals, plants and bacteria. Most commercial debriding enzymes are derived from cows, including the following four enzymes. Fibrinolysin is a plasma enzyme which, after being activated, attacks fibroin components in blood clots and exudates. Deoxyribonuclease is a pancreatic enzyme that specifically attacks nucleoprotein components of purulent exudates. These two enzymes are combined in a product known as ELASE® that finds use mostly in Europe. Trypsin and chymotrypsin are fairly nonspecific pancreatic enzymes, but they sever (i.e., cleave) substrate protein backbones at specific amino acid residues. Enzymes from other animals include krillase, a protease derived from Antarctic krill.

Tropical fruit-bearing plants provide a second source of debridement enzymes. Bromelain is a group of enzymes from the stem of pineapple plants; it includes three cysteine proteases (i.e., they have the cysteine amino acid at their active site) and the mixture breaks down tissue in the range of pH 5.5-8.5. Papain is a nonspecific cysteine protease from papaya latex that breaks down a wide variety of substances in necrotic (i.e., dead or nonviable) tissues over a wide pH range—pH 3.0-12.0; it can degrade fibroin, collagen and elastin. Ficin is a non-specific cysteine protease of similar operating pH characteristics, and is derived from a plant latex, that of the ficus (fig) plant; ficin preferentially cleaves proteins at tyrosine and phenylalanine residues.

Bacterial cultures are yet another source of debridement enzymes. Subtilisins are mixtures of relatively nonspecific, water-soluble serine proteases (i.e., they have serine at their active site), which break down necrotic tissues optimally at pH 6.0-6.8. They are derived from *Bacillus subtilis* bacteria. Collagenases are enzymes that attack collagen and require the presence of certain metal ions, i.e., they are metallopeptidases; commercially they are derived from *Clostridium histolyticum*. Vibriolysin is another very active collagen-attacking metallopeptidase, and it is derived from *Vibrio proteolyticus* bacteria. Thermolysin is a bacterial debridement enzyme that acts nonspecifically with outstanding productivity even at 80° C.; it is derived from *Bacillus thermoproteolyticus*, and requires the presence of normal wound healing cofactors such as zinc and calcium ions.

The use of thermolysin for debridement was taught by Shi et al. in US Patent Publication Nos. 2003/019863 1 A1 and 2003/0198632 A1. Streptokinase (a fibrinogen activating protease from *streptococcus*) and streptodornase (streptococcal deoxyribonuclease) are additional examples of bacterial proteases with value for debridement purposes.

Proteases from other types of organisms can also be useful. For instance, proteinase K is derived from the mold *Tritirachium album limber*. It is a senile endopeptidase that has subtilisin-like activity, and which breaks down the structural protein keratin and other proteins under alkaline conditions (e.g., pH 8 or pH 9); it is used for instance to digest cells so that their DNA and RNA can be recovered.

Several papain-urea based commercial debridement ointments are in common use to remove dead cells as part of the wound-cleaning process, including ACCUZYME®, ETHEZYME™ and PANAFIL®. According to product literature, urea is combined with papain to provide two supplementary actions: 1) to expose by solvent action the activators of papain (sulfhydryl groups) which are always present, but not necessarily accessible, in non-viable tissue or debris of lesions; and 2) to denature the non-viable protein matter in lesions and thereby render it more susceptible to enzymatic digestion. In pharmacologic studies involving digestion of beef powder, it has been shown that the combination of papain and urea produced nearly twice as much digestion as papain alone.

ACCUZYME® (HealthPoint, Fort Worth, Tex.) enzymatic debriding ointment (HealthPoint, Forth Worth, Tex.) contains papain, USP ($8.3 \times 10^5$ USP units of activity per gram) and urea, USP 10% in a hydrophilic ointment base composed of emulsifying wax, fragrance, glycerin, isopropyl palmitate, lactose, methylparaben, potassium phosphate monobasic, propylparaben, and purified water. ACCUZYME® SE is a patent-pending delivery system that contains the same active ingredients and same units of activity as ACCUZYME®.

ETHEZYME™ (Ethex Corporation, St. Louis, Mo.) is another enzymatic debridement ointment. Each gram of ETHEZYME™ contains papain, USP ($1.1 \times 10^6$ USP units of activity) and 100 mg urea, USP. Each gram of ETHEZYME™ 830 contains papain, USP ($8.3 \times 10^5$ USP units of activity) and 100 mg urea, USP. Each gram of ETHEZYME™ 650 contains papain, USP ($6.5\ 10^5$ USP units of activity) and 100 mg urea, USP. All are in a hydrophilic ointment base composed of purified water, USP, edetate disodium, USP, emulsifying wax, NF, fragrance, glycerin, USP, isopropyl palmitate, NF, methylparaben, NF, polyoxyl 40 stearate, NF, potassium phosphate monobasic, USP, propylparaben, NF and tocopherols, mixed. All are indicated for debridement of necrotic tissue and liquefaction of pus in acute and chronic lesions such as decubitus, varicose and diabetic ulcers, burns, postoperative wounds, pilonidal cyst wounds, carbuncles and miscellaneous traumatic or infected wounds. All are applied directly to the lesion and covered with an appropriate dressing. Daily or twice daily changes are preferred.

PANAFIL® Ointment (HealthPoint, Fort Worth, Tex.) is an enzymatic healing-debriding ointment which contains standardized Papain, USP, Urea USP 10% and Chlorophyllin Copper Complex Sodium 0.5% in a hydrophilic base composed of Purified Water, USP; Propylene Glycol, USP; White Petrolatum, USP; Stearyl Alcohol, NF; Polyoxyl 40 Stearate, NF; Sorbitan Monostearate, NF; Boric Acid, NF; Chlorobutanol (Anhydrous), NF as a preservative; Sodium Borate, NF.

Some enzyme-free wound dressings have employed trace amounts of urea compounds as preservatives, thus Woller et al. in U.S. Pat. No. 5,902,600 teach the use of 0.05 to 0.50 weight percent imidurea—an oligomeric derivative of urea—as a preservative for hydrated glycerin-based wound dressings.

Normal cell and tissue is growth-limited. When growth becomes unregulated, disorders of abnormal cell proliferation result. A neoplasm is a collection of cells growing in an unregulated way. Neoplasms can be either benign or malignant (cancerous). Cancer is a class of diseases or disorders characterized by uncontrolled division of cells and the ability of these to spread, either by direct growth into adjacent tissue through invasion, or by implantation into distant sites by metastasis (where cancer cells are transported through the bloodstream or lymphatic system). In many cancers, the cells clump together to form solid tumors, but in some the cells are dispersed around the blood stream (leukemia) or the lymphatic system (lymphoma).

The goal of cancer therapy is to selectively destroy these abnormal proliferating cells, leaving normal cells unharmed, since even a small number of remaining cancerous cells can lead to recurrence, metastasis, and death. Selectivity at the cellular level is particularly desired for the destruction of highly invasive cancers such as breast cancers in which malignant cells have become closely associated and convoluted with bone mass or other anatomical structures, thereby frustrating attempts at complete removal by surgical means. Selectivity need not be absolute, i.e., in many cases some destruction of normal cells by a therapeutic method would be tolerable if the method removed cancer cells extensively and preferentially.

Ideally, after removal of cancerous tissues, the affected site would be replenished with healthy tissue. However, removal of tumors by common therapeutic methods often results in the formation of scar tissue. This scar tissue acts as a barrier to re-entry by normal tissue, with consequent morphological disfigurement of the affected tissues even after an effective cancer treatment. Thus the use of non-scarring therapies is desired.

US Patent Publication No. 2003/0026794 A1 (Fein) discloses a method of treating skin conditions by providing compositions containing enzymes to selectively remove specific layers of skin. The depth of skin removed (that is, vertical surface treated) is regulated by the type and concentration of enzyme or enzymes in the composition. The surface area of skin removed is regulated by the area of topical application. Conditions treatable by the method are said to include, for example, age-related conditions such as lines and wrinkles, infections, pigmentary disorders, neoplasms affecting the skin, follicular disorders such as acne, and hyperkeratotic disorders such as warts.

U.S. Pat. No. 6,811,788 (Yu) teaches a method for treating a neoplasm in a mammal, comprising in situ administration of an effective amount of a hapten and a coagulation agent(s) that causes coagulation of the neoplasm, wherein the hapten is trinitrophenol and the coagulation agents are a combination of hydrogen peroxide and ethanol, and whereby an immune response is generated against the neoplasm. Yu discloses the optional addition of papain to serve as an immune response potentiator, as well as the optional addition of proteinase K, to serve as a coagulation lysing agent.

There is an ongoing need for improved treatment methods for diseases and disorders of abnormal cell proliferation, and in particular, the need for selective therapies for neoplastic diseases, including benign and malignant neoplasms and other forms of cancer.

It is therefore an object of the present to provide compositions and methods of selective enzymatic debridement for the treatment of diseases and disorders of abnormal cell proliferation, including benign and malignant neoplasms and other forms of cancer.

SUMMARY OF THE INVENTION

The present invention relates to a method for the treatment of disorders characterized by abnormal cell proliferation, including benign and malignant neoplasms and other cancers, which includes administration of an effective amount of one or more debridement enzymes and a denaturant to a subject in need thereof. The methods of the present invention permits selective destruction of neoplastic tissue while leaving normal tissue largely intact.

In one aspect, the present invention is a method of treating a neoplasm in a subject by administering an effective amount of one or more debridement enzymes and a denaturant.

In one embodiment, the neoplasm is a neoplasm of the abdomen, bone, breast, digestive system, endocrine gland, eye, brain, head, neck, blood, nervous system, pelvis, soft tissue, spleen, heart, lung, thymus or urogenital system.

In a particular embodiment, the neoplasm is not a neoplasm or disorder of the skin.

In one embodiment, the denaturant is administered in combination or alternation with the enzyme. In certain embodiments, the denaturant is administered in combination with the enzyme. In other embodiments, the denaturant is administered prior to or after administration of the debridement enzyme.

In one embodiment, the debridement enzyme is selected from the group consisting of plasma enzymes, pancreatic enzymes, cysteine proteases, serine proteases, and metallopeptidases. In specific embodiments, the enzyme is selected from the group consisting of fibrinolysin, desoxyribonuclease, trypsin, chymotrypsin, krillase, bromelain, papain, ficin, subtilisins, proteinase K, collagenases, vibriolysin, thermolysin, streptokinase, streptodornase, and proteolytic enzymes excreted by maggots.

In one particular embodiment, the debridement enzyme is papain.

In a specific embodiment, the denaturant is urea.

In a particular embodiment, the present invention is a method of treating a neoplasm in a subject by administering an effective amount of papain and urea.

In a particularly preferred embodiment, the present invention is a method of treating a neoplasm of the breast by administering an effective amount of a composition comprising one or more debridement enzymes and a denaturant. In certain embodiments, the invention provides a method of treating a neoplasm of the breast by administering an effective amount of papain and urea. The breast neoplasm may be benign or malignant, invasive or non-invasive.

In one embodiment, the method involves administration of one or more debridement enzymes and a denaturant in a pharmaceutically acceptable carrier.

In a particular embodiment, the debridement enzyme is administered in a dose of from about $1 \times 10^4$ to about $1 \times 10^8$ USP per gram; or from about $1 \times 10^5$ to about $1 \times 10^7$ USP per gram; or from about $5 \times 10^5$ to about $5 \times 10^6$ USP per gram or at about $1.1 \times 10^6$ USP per gram.

In another particular embodiment, the denaturant is a chemical compound that is present from about 0.1 to about 40 weight percent; or from about 2 to about 30 weight percent; or from about 5 to about 20 weight percent; or from about 7 to about 15 weight percent; or about 10 weight percent; or over about 15 weight percent; or from about 1 to about 5 weight percent.

In one embodiments the debridement enzyme retains at least about 10%, at least about 30%, at least about 50%, at least about 65%, at least about 80%, at least about 90%, at least about 95%, or at least about 99% of its activity at the concentrations at which the denaturant is provided.

In another embodiment, the method further provides administration of an enzyme stabilizing compound in combination or alternation with the enzyme or denaturant. In particular embodiments, the stabilizing compound is selected from the group consisting of sugars, polyhydric alcohols, and certain salts. In particular embodiments, the stabilizing compound is selected from monosaccharides, disaccharides, oligosaccharides, pyranose sugars, furanose sugars, glucose, lactose and sucrose. In particular embodiments, the stabilizing compound is glycerol, pentaerythritol, 0-phosphate derivatives of any of those compounds and 2,3-bisphosphoglycerate In certain embodiments, the stabilizing compound is selected from manganese salts, iron salts, cobalt salts, nickel salts, copper salts, zinc salts, magnesium salts, calcium salts, sodium salts, potassium salts, and ammonium salts.

In a particular embodiment, the method involves administration of (i) papain, optionally at $1.1 \times 10^6$ USP per gram; (ii) 10 weight percent urea; and (iii) up to 50 weight percent of an enzyme stabilizing compound which is optionally lactose.

In another particular embodiment, the method involves administration of (i) proteinase K; (ii) a denaturant selected from the group consisting of urea, sodium dodecyl sulfate and ethylenediaminetetraacetic acid (EDTA); and (iii) glucose.

In yet another particular embodiment, the method involves administration of (i) porcine trypsin that has been modified by reductive methylation; (ii) a denaturant selected from the group consisting of the group consisting of 1M urea, 0.1% sodium dodecyl sulfate, 10% acetonitrile, and 2M guanidine hydrochloride; and (iii) glucose, together in a pharmaceutical formulation that has a pH of from about 7-9.

In a further embodiment the method involves further administration of one or more of the following: (i) a supplemental agent that minimizes damage to healthy normal cells from compounds released by dying cells, wherein the agent is optionally sodium copper chlorophyllin; (ii) a cofactor optionally selected from the group consisting of ATP, ADP, NAD, NADH, NADP, NADPH, oxidized and reduced flavins, folic acid, and folic acid derivatives, wherein the range of the stoichiometric ratio of moles of cofactor administered to moles of debridement enzyme administered is optionally 0.1 to 10.0, 0.3 to 3.0, or 1.0; (iii) excipients optionally selected from the group consisting of emulsifying wax fragrance, isopropyl palmitate, lactose, methylparaben, potassium phosphate monobasic, propylparaben, and purified water; or (iv) a buffer to maintain the pH within the operating range of the debridement enzyme.

In a further embodiment, the method is used before, after, or concomitantly with another form of cancer therapy including, without limitation, surgical, chemotherapeutic, or irradiation therapy.

The method used to administer the composition of the present invention may vary and may include, without limitation, topical, oral, or parenteral (e.g., intravenous) administration.

In a particular embodiment, the method involves intravenous administration.

In one embodiment, the method involves administration by cannulation.

In further embodiment the method disclosed herein employs a biodegradable surgical dressing that comprises the debridement enzyme and the denaturant.

DETAILED DESCRIPTION OF THE INVENTION

Figure 1:
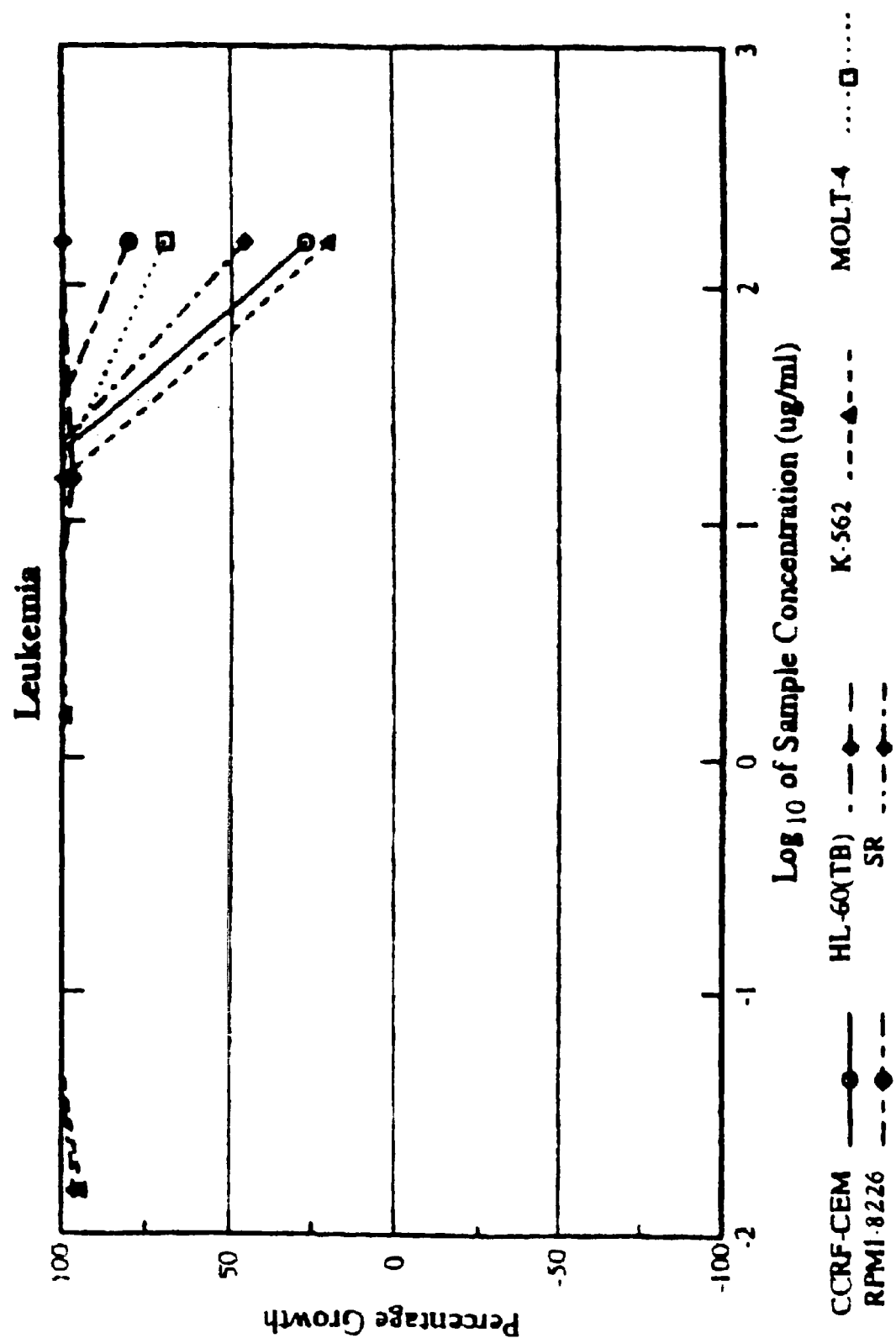
FIG. 1 illustrates the effect of exemplary enzymatic compositions on the growth rate of various leukemia cell lines over a 48 hour period when presented at dilutions representing 0.013, 0.13, 1.30, 13, and 130 USP units of papain enzymatic activity per ml of cell culture medium. These enzymatic activities correspond to papain/urea cream sample concentrations of −1.8, −0.8, 0.2, 1.2 and 2.2 ug/ml.

It has been discovered that neoplastic lesions can be preferentially destroyed by the combination of a debridement enzyme and a denaturant while leaving normal cells largely intact, and while leaving little or no scar tissue. It is contemplated that the methods disclosed herein will be used to treat neoplasms and other disorders of abnormal cell proliferation.

As used herein, the term neoplasm refers to an abnormal growth of tissue. A neoplasm may be benign or malignant. Generally, a malignant neoplasm is referred to as a cancer. Cancers differ from benign neoplasms in the ability of malignant cells to invade other tissues, either by direct growth into adjacent tissue through invasion or by implantation into distant sites by metastasis (i.e., transport through the blood or lymphatic system). The methods of the present invention are suitable for the treatment of benign and malignant neoplasms (cancer).

As defined herein a superficial neoplasm is one located on the outer surface of the body that has confined itself and not spread to surrounding tissues or other parts of the body. An internal neoplasms located on an internal organ or other internal part of the body. An invasive neoplasm is a neoplasm that has started to break though normal tissue barriers and invade surrounding areas, e.g., an invasive breast cancer that has spread beyond the ducts and lobules A non-exclusive list of the types of neoplasms contemplated for treatment by the method disclosed herein includes the following categories:

(a) abdominal neoplasms including peritonealneoplasms and retroperitoneal neoplasms;

(b) bone neoplasms including femoral neoplasms, skull neoplasms, jaw neoplasms, manibular neoplasms, maxillary neoplasms, palatal neoplasms, nose neoplasms, orbital neoplasms, skull base neoplasms, and spinal neoplasms;

(c) breast neoplasms including male breast neoplasms, breast ductal carcinoma, and phyllodes tumor;

(d) digestive system neoplasms including biliary tract neoplasms, bile duct neoplasms, common bile duct neoplasms, gall bladder neoplasms, gastrointestinal neoplasms, esophegeal neoplasms, intestinal neoplasms, cecal neoplasms, appendiceal neoplasms, colorectal neoplasms, colorectal adenomatous polyposis coli, colorectal Gardner Syndrome, colonic neoplasms, colonic adenomatous polyposis coli, colonic Gardner Syndrome, sigmoid neoplasms, hereditary nonpolyposis colorectal neoplasms, rectal neoplasms, anus neoplasms, duodenal neoplasms, ileal neoplasms, jejunal neoplasms, stomach neoplasms, liver neoplasms, liver cell adenoma, hepatocellular carcinoma, pancreatic neoplasms, islet cell adenoma, insulinoma, islet cell carcinoma, gastrinoma, glucagonoma, somatostatinoma, vipoma, pancreatic ductal carcinoma, and peritoneal neoplasms;

(e) endocrine gland neoplasms including adrenal gland neoplasms, adrenal cortex neoplasms, adrenocortical adenoma, adrenocortical carcinoma, multiple endocrine neoplasia, multiple endocrine neoplasia type 1, multiple endocrine neoplasia type 2a, multiple endocrine neoplasia type 2b, ovarian neoplasms, granulosa cell tumor, luteoma, Meigs' Syndrome, ovarian Sertoli-Leydig cell tumor, thecoma, pancreatic neoplasms, paraneoplastic endocrine syndromes, parathyroid neoplasms, pituitary neoplasms, Nelson Syndrome, testicular neoplasms, testicular Sertoli-Leydig cell tumor, and thyroid neoplasms;

(f) eye neoplasms including conjunctival neoplasms, orbital neoplasms, retinal neoplasms, retinoblastoma, uveal neoplasms, choroid neoplasms, and iris neoplasms;

(g) brain, head and neck neoplasms including esophageal neoplasms, facial neoplasms, eyelid neoplasms, mouth neoplasms, gingival neoplasms, oral leukoplakia, hairy leukoplakia, lip neoplasms, palatal neoplasms, salivary gland neoplasms, parotid neoplasms, sublingual gland neoplasms, submandibular gland neoplasms, tongue neoplasms, otorhinolaryngologic neoplasms, ear neoplasms, laryngeal neoplasms, nose neoplasms, paranasal sinus neoplasms, maxillary sinus neoplasms, pharyngeal neoplasms, hypopharyngeal neoplasms, nasopharyngeal neoplasms, nasopharyngeal neoplasms, oropharyngeal neoplasms, tonsillar neoplasms, parathyroid neoplasms, thyroid neoplasms, and tracheal neoplasms;

(h) hematologic neoplasms including bone marrow neoplasms;

(i) nervous system neoplasms including central nervous system neoplasms, brain neoplasms, cerebral ventricle neoplasms, choroid plexus neoplasms, choroid plexus papilloma, infratentorial neoplasms, brain stem neoplasms, cerebellar neoplasms, neurocytoma, pinealoma, supratentorial neoplasms, hypothalamic neoplasms, pituitary neoplasms, Nelson Syndrome, cranial nerve neoplasms, optic nerve neoplasms, optic nerve glioma, acoustic neuroma, neurofibromatosis 2, nervous system paraneoplastic syndromes, Lambert-Eaton myasthenic syndrome, limbic encephalitis, transverse myelitis, paraneoplastic cerebellar degeneration, paraneoplastic polyneuropathy, peripheral nervous system neoplasms, cranial nerve neoplasms, acoustic neuroma, and optic nerve neoplasms;

(j) pelvic neoplasms;

(k) skin neoplasms including acanthoma, sebaceous gland neoplasms, sweat gland neoplasms and basal cell carcinoma;

(l) soft tissue neoplasms including muscle neoplasms and vascular neoplasms;

(m) splenic neoplasms;

(n) thoracic neoplasms including heart neoplasms, mediastinal neoplasms, respiratory tract neoplasms, bronchial neoplasms, lung neoplasms, bronchogenic carcinoma, non-small-cell lung carcinoma, pulmonary coin lesion, Pancoasts's Syndrome, pulmonary blastoma, pulmonary sclerosing hemangioma, pleural neoplasms, malignant pleural effusion, tracheal neoplasms, thymus neoplasms, and thymoma;

(o) urogenital neoplasms including female genital neoplasms, fallopian tube neoplasms, uterine neoplasms, cervix neoplasms, endometrial neoplasms, endometrioid carcinoma, endometrial stromal tumors, endometrial stromal sarcoma, vaginal neoplasms, vulvar neoplasms, male genital neoplasms, penile neoplasms, prostatic neoplasms, testicular neoplasms, urologic neoplasms, bladder neoplasms, kidney neoplasms, renal cell carcinoma, nephroblastoma, Denys-Drash Syndrome, WAGR Syndrome, mesoblastic nephroma, ureteral neoplasms and urethral neoplasms;

(p) and additional cancers including renal carcinoma, lung cancer, melanoma, leukemia, Barrett's esophagus, metaplasia pre-cancer cells.

In a particular embodiment, the method of the present invention is used to treat neoplasms that are not neoplasms or disorders of the skin.

In a particular embodiment, the method of the present invention can be used to treat neoplasms of the breast, including in situ breast cancers and invasive breast cancers. In situ breast cancer is a term that refers to cancer in which the breast cancer cells have remained contained within their place of origin, i.e., they haven't invaded breast tissue around the duct or lobule. These include, e.g., ductal carcinoma in suit (DCIS) and lobular carcinoma in suit (LCIS). Invasive or infiltrating breast cancers are those that have invading the surrounding tissues. These include, without limitation, invasive ductal carcinoma (IDC) and invasive lobular carcinoma (LCIS). Other forms of breast cancer suitable for treatment according to the present invention include Inflammatory breast cancer, medullary carcinoma, mucinous carcinoma, Paget disease of the nipple, Phyllodes tumor and tubular carcinoma. Other rare tumors of the breast include angiosarcoma, squamous cell cancer and lymphoma.

Diseases of abnormal cell proliferation other than cancer can be treated according to the present invention including, without limitation, benign tumors, atherosclerosis, restenosis. cutaneous mastocytosis (CM), Urticaria pigmentosa, IgA nephropathy, membranoproliferative glomerulonephritis (GN), lupus nephritis, diabetic nephropathy and rheumatoid arthritis, as well as other diseases associated with abnormal cell proliferation known to those skilled in the art.

The method of the present invention involves treatment of a disease or disorder of abnormal cell proliferation, such as a benign or malignant neoplasm or other form of cancer, by administration of one or more debridement enzymes and a denaturant. The denaturant may be administered jointly with, concurrently with, prior to, or after the administration of the debridement enzyme.

Debridement enzymes suitable for use in the method includes those described in the Background of the Invention, as any of the following non-limiting examples: plasma enzymes, pancreatic enzymes, cysteine proteases, serine proteases, and metallopeptidases, and permutations of them. For example, the debridement enzyme may be selected from the group consisting of fibrinolysin, deoxyribonuclease, trypsin, chymotrypsin, krillase, bromelain, papain, ficin, subtilisins, proteinase K, collagenases, vibriolysin, thermolysin, streptokinase, streptodornase, and proteolytic enzymes excreted by maggots (e.g., L. sericata larval excretory/secretory products (ES) as described in Horobin et al., J Invest Dermatol. June 2006; 126(6):1410-8) or porcine trypsin that has been modified by reductive methylation.

Denaturing can be understood as follows. A protein is a long, ribbon-like molecule that has an optimal coiling configuration which often includes and relies upon some cross-links to itself. When the protein uncoils (i.e., denatures) and or uncross-links to some degree and does not afterward return to the preferred coiling pattern, then it cannot carry out its usual function: denatured enzymes cannot catalyze to a significant degree; denatured structural proteins are mechanically compromised; and denatured adhesion proteins may no longer adhere correctly. Denaturing can arise by melting (by heat), by chemical action (e.g., by oxidizers), by fully or partially dissolving the protein (by detergents, solvents, salts, urea, or other agents), or by altering distribution of electrical charges on the protein (e.g., by use of strong acids or bases). For denaturation purposes, compounds such as urea are typically employed in molar or multi-molar proportions.

Denaturants suitable for use in the method include any, but are not limited to: urea; a salt or acid in which the anion is $I^-$, $ClO_4^-$, or $SCN^-$; a salt or base in which the cation is $Li^+$, $Mg^{++}$, $Ca^{++}$, $Ba^{++}$, or guanidinium; lactic acid; citric acid; an aliphatic alcohol; 13-mercaptoethanol; a detergent; sodium dodecyl sulfate; formaldehyde; acetone; acetonitrile; dimethylsulfoxide; dimethylformamide; propylene carbonate; ethylene carbonate; a drug containing a heavy metal; a drug containing silver; a drug containing mercury; a drug containing lead; silver sulfadiazine; gentamicin; and penicillin. Examples of silver-containing drugs include silver nitrate, silver protein binders, colloidal silver, and silver-containing topical burn medications. Examples of mercury-containing drugs include mercurochrome, mercuric nitrate, mercuric acetate, thimerosal, phenyl mercuric acetate, merbromin, and mercuric oxide yellow. Examples of lead-containing drugs includer certain Ayurvedic medications and other ethnic medications, see e.g., discussion at www.cdc.gov/mmwr/preview/mmwrhtml/mm5326a3.htm.

Additional denaturants contemplated the method are metal scavengers, which can remove metal ions or metal centers that stabilize the preferred conformation of the proteins. Non-limiting examples of metal scavengers include crown ethers of which an example is 15-crown-S circular polyethylene oxide, crown amines; polyethers of which an example is polyethylene oxide; polyamines of which an example is polyethylene amine; cryptands; chelators; and ligands of which an example is ethylenediaminetetraacetic acid (EDTA).

Additional denaturants contemplated for the method include strong acids, strong bases, and heat such as the application of infrared heat to a lesion during treatment. A strong acid is defined here as an acid having a $pK_a$ larger than the $pK_a$ required for acidic denaturation of a target protein under the conditions of treatment, e.g., an acid with a $pK_a$ less than about 4. Non-limiting examples of strong acids include hydrochloric, phosphoric, and sulfuric acids. A strong base is defined here as a base having a $pK_a$ lower than the $pK_a$ required for basic denaturation of a target protein under the conditions of treatment, e.g., a base with a $pK_a$ greater than about 10. Nonexclusive examples of strong bases include sodium hydroxide, potassium hydroxide, and sodium carbonate. Still other denaturants contemplated for the method disclosed herein include applied heat, wherein heat is defined as possessing at least the quantity of thermal energy that is required to denature a target protein under the conditions of treatment.

In one embodiments the debridement enzyme retains at least about 10%, 30%, 50%, 65%, 80%, 90%, 95%, or 99% of its activity at the concentrations at which the denaturant is provided.

In another embodiment, the method involves further administration of an enzyme stabilizing compound wherein the stabilizing compound is optionally selected from the group consisting of sugars, monosaccharides, disaccharides, oligosaccharides, pyranose sugars, furanose sugars, glucose, lactose, sucrose, glycerol, pentaerythritol, polyhydric alcohols, O-phosphate derivatives of any of those compounds, 2,3-bisphosphoglycerate, manganese salts, iron salts, cobalt salts, nickel salts, copper salts, zinc salts, magnesium salts, calcium salts, sodium salts, potassium salts, and ammonium salts.

In a particular embodiment, the method involves administration of (i) papain, optionally at $1.1 \times 10^6$ USP per gram; 10 weight percent urea; and (iii) up to 50 weight percent of an enzyme stabilizing compound which is optionally lactose.

In another particular embodiment, the method involves administration of (i) proteinase K; (ii) a denaturant selected from the group consisting of urea, sodium dodecyl sulfate and ethylenediaminetetraacetic acid (EDTA); and (ii) glucose.

In yet another particular embodiment, the method involves administration of (i) porcine trypsin that has been modified by reductive methylation; (ii) a denaturant selected from the group consisting of the group consisting of 1M urea, 0.1% sodium dodecyl sulfate, 10% acetonitrile, and 2M guanidine hydrochloride; and (iii) glucose, together in a pharmaceutical formulation that has a pH of from about 7-9.

In a further embodiment the method involves administration of one or more debridement enzymes in a hydrophilic ointment, with ointment is administered before, concomitantly, after or in the same formulation with one of the following: (i) a supplemental agent that minimizes damage to healthy normal cells from compounds released by dying cells, wherein the agent is optionally sodium copper chlorophyllin; (ii) a cofactor optionally selected from the group consisting of ATP, ADP, NAD, NADH, NADP, NADPH, oxidized and reduced flavins, folic acid, and folic acid derivatives, wherein the range of the stoichiometric ratio of moles of cofactor administered to moles of debridement enzyme administered is optionally 0.1 to 10.0, 0.3 to 3.0, or 1.0; (iii) excipients optionally selected from the group consisting of emulsifying wax fragrance, isopropyl palmitate, lactose, methylparaben, potassium phosphate monobasic, propylparaben, and purified water; (iv) a buffer to maintain the pH within the operating range of the debridement enzyme.

The method of the present invention can be used before, after, or concomitantly with another cancer therapy such as surgical, chemotherapeutic, or irradiation means. Each of these therapies is well known in the art.

The method of the present invention can be used before, after or concomitantly with chemotherapy. Representative, non-limiting examples of chemotherapeutic agents that can be used in combination with the compositions and methods of the present invention include: (i) anti-proliferative agents such as adjuncts (e.g., levamisole, gallium nitrate, granisetron, sargramostim strontium-89 chloride, filgrastim, pilocarpine, dexrazoxane, and ondansetron); (ii) androgen inhibitors (e.g., flutamide and leuprolide acetate); (iii) antibiotic derivatives (e.g., doxorubicin, bleomycin sulfate, daunorubicin, dactinomycin, and idarubicin); (iv) antiestrogens (e.g., tamoxifen citrate and analogs thereof, nonsteroidal antiestrogens such as toremifene, droloxifene and roloxifene); (v) antimetabolites (e.g., fluorouracil, fludarabine phosphate, floxuridine, interferon alfa-2b recombinant, methotrexate sodium, plicamycin, mercaptopurine, and thioguanine); (vi) cytotoxic agents (e.g., doxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci) (vi) hormones (e.g., medroxyprogesterone acetate, estradiol, megestrol acetate, octreotide acetate, diethylstilbestrol diphosphate, testolactone, and goserelin acetate); (vii) immunodilators (e.g., aldesleukin); (viii) nitrogen mustard derivatives (e.g., melphalan, chlorambucil, mechlorethamine, and thiotepa); (ix) steroids (e.g., betamethasone sodium phosphate and betamethasone acetate); and (x) antineoplastic agents (e.g., paclitaxel or doxorubicin).

Additional suitable chemotherapeutic agents include alkylating agents, antimitotic agents, plant alkaloids, biologicals, topoisomerase I inhibitors, topoisomerase II inhibitors, and synthetics. Representative alkylating agents include asaley, AZQ, BCNU, busulfan, bisulphan, carboxyphthalatoplatinum, CBDCA, CCNU, CHIP, chlorambucil, chlorozotocin, cis-platinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864. *AntiCancer Agents by Mechanism*, http://dtp.nci.nih.gov/docs/cancer/searches/standard_mechanism_list.html, Apr. 12, 1999.

Representative antimitotic agents include allocolchicine, Halichondrin M, colchicine, colchicine derivatives, dolastatin 10, maytansine, rhizoxin, paclitaxel derivatives, paclitaxel, thiocolchicine, trityl cysteine, vinblastine sulfate, and vincristine sulfate.

Representative plant alkaloids include actinomycin D, bleomycin, L-asparaginase, idarubicin, vinblastine sulfate, vincristine sulfate, mitramycin, mitomycin, daunorubicin, VP-16-213, VM-26, navelbine and taxotere. *Approved Anti-Cancer Agents*, http://ctep.info.nih.gov/handbook/HandBook Text/fda_agent.htm, Jun. 18, 1999.

Representative biologicals include alpha interferon, BCG, G-CSF, GM-CSF, and interleukin-2. *Approved Anti-Cancer Agents*, http://ctep.info.nih.gov/handbook/HandBookText/fda_agent.htm, Jun. 18, 1999.

Representative topoisomerase I inhibitors include camptothecin, camptothecin derivatives, and morpholinodoxorubicin. *AntiCancer Agents by Mechanism*, http://dtp.nci.nih.gov/docs/cancer/searches/standar_mechanism_list.html, Apr. 12, 1999.

Representative topoisomerase II inhibitors include mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16. *AntiCancer Agents by Mechanism*, http://dtp.nci.nih.gov/docs/cancer/searches/standard_mechanism_list.html, Apr. 12, 1999.

Representative synthetics include hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium. *Approved Anti-Cancer Agents*, http://ctep.info.nih.gov/handbook/HandBookText/fda_agen.htm, Jun. 18, 1999.

Representative antibodies include monoclonal antibodies directed to proliferating cells such as Rituximab (anti-CD20) for B-cell tumors and herceptin.

Other compounds well known in the art for treating nonmalignant disorders of abnormal cell proliferation can also be used together with the compositions and methods of the present invention.

The method used to administer the composition of the present invention may vary and include any suitable mode of administration, as described further below under Pharmaceutical Formulations and Administration.

In one aspect, the present invention is a composition including an effective amount of one or more debridement enzymes in combination with a denaturant. The debridement enzyme may be, for example, any of the debridement enzymes identified above with respect to the method, including but not limited to pancreatic enzymes, plasma enzymes, cystein proteases, serine proteases, metallopeptidases and permutations of them. In a particular embodiment, the composition includes two or more debridement enzymes. In a further particular embodiment, the compositions includes three or more debridement enzymes. In one embodiment, one of the two or optionally three or more debridement enzymes is papain. Papain is active over a wide pH range, i.e., from 3 to 12, which renders papain suitable for combination with acidic and basic denaturants. Nor is papain inhibited by penicillin or sulfonamide drugs.

The composition of the present invention includes a denaturant. Denaturants contemplated for the composition of the present invention include, but are not limited to the following: urea; a salt or acid in which the anion is $I^-$, $ClO_4^-$, or $SCN^-$; a salt or base in which the cation is $Li^+$, $Mg^{++}$, $Ca^{++}$, $Ba^{++}$, or guanidinium; lactic acid; citric acid; an aliphatic alcohol; 13-mercaptoethanol; a detergent; sodium dodecyl sulfate; formaldehyde; acetone; acetonitrile; dimethylsulfoxide; dimethylformamide; propylene carbonate; ethylene carbonate; a drug containing a heavy metal; a drug containing silver; a drug containing mercury; a drug containing lead; silver sulfadiazine; gentamicin; and penicillin.

Additional denaturants contemplated for the compositions herein are metal scavengers, which can remove metal ions or metal centers that stabilize the preferred conformation of the proteins. Non-limiting examples of metal scavengers include crown ethers of which an example is 15-crown-5 circular polyethylene oxide, crown amines; polyethers of which an example is polyethylene oxide; polyamines of which an example is polyethylene amine; cryptands; chelators; and ligands of which an example is ethylenediaminetetraacetic acid (EDTA).

Additional denaturants contemplated for the compositions herein include strong acids, strong bases, and heat such as the application of infrared heat to a lesion during treatment. A strong acid is defined here as an acid having a $pK_a$ larger than the $pK_a$ required for acidic denaturation of a target protein under the conditions of treatment, e.g., an acid with a $pK_a$ less than about 4. Nonlimiting examples of strong acids include hydrochloric, phosphoric, and sulfuric acids. A strong base is defined here as a base having a $pK_a$ lower than the $pK_a$ required for basic denaturation of a target protein under the conditions of treatment, e.g., a base with a $pK_a$ greater than about 10. Nonexclusive examples of strong bases include sodium hydroxide, potassium hydroxide, and sodium carbonate. Still other denaturants contemplated for the compositions herein include applied heat, wherein heat is defined as possessing at least the quantity of thermal energy that is required to denature a target protein under the conditions of treatment.

In a preferred embodiment, the denaturant is urea. Urea may act in combination with one or more debridement enzymes, such as papain, to provide a synergistic effect. A particular embodiment of the compositions disclosed herein is the combination of a debridement enzyme with a denaturant whereby at that concentration of the denaturant the debridement enzyme retains at least 10% of the native activity of debridement enzyme, more particularly at least 30% of the native activity, still more particularly at least 50% of the native activity, yet more particularly at least 65% of the native activity, even more particularly at least 80% of the native activity, more particularly at least 90% of the native activity, more particularly at least 95% of the native activity, and still more particularly at least 99% of the native activity.

Stabilizing compounds are common excipients for formulations of enzymes, and they stabilize the preferred conformation of the enzyme. Non-limiting examples of stabilizing compounds that may be present in the composition include sugars, including but not limited to pyranose sugars and furanose sugars, mono-, di- and oligosaccharides, as well as other polyhydric alcohols, and including 0-phosphate derivatives of any of those compounds. Examples include glucose, lactose, sucrose, glycerol, pentaerythritol, polyhydric alcohols, and their 0-phosphate derivatives, including 2,3-bisphosphoglycerate. Non-limiting examples of stabilizing compounds also include salts, particularly compounds such as manganese salts, iron salts, cobalt salts, nickel salts, copper salts, zinc salts, magnesium salts, calcium salts, sodium salts, potassium salts, and ammonium salts.

The compositions disclosed herein may also include a supplemental agent that minimizes damage to healthy normal cells from compounds released by dying cells. In a particular embodiment, the composition includes sodium copper chlorophyllin. Sodium copper chlorophyllin is included in certain commercial papain/urea compositions because it appears to have a wound-healing effect: it is an agglutinin and anti-inflammatory substance; it also reduces odor from the wound. Chlorophyllin also enhances the selectivity of the enzyme, because chlorophyllin protects healthy cells from the toxic effect of substances emitted from the dead tissue. Other supplemental agents include antioxidants such as carotene, lycopene, a form of vitamin A such as retinol, BHT, vanillin, tannins and other antioxidants such as are known in the art for treating and preventing effects of cancer.

Digestion and healing by formulations of the invention may be assisted by the use of polar aprotic solvents such as acetone; acetonitrile; dimethylsulfoxide; dimethylformamide; propylene carbonate and ethylene carbonate that can permeate skin and other tissues, and which enable the permeation of other compounds such as antioxidants through tissues with them.

The action of formulations of the present invention may also be assisted by combinations that include an enzyme capable of cleaving the backbone of a polysaccharide, where the combination is in alternation, in parallel, or in a mutual formulation. The degradation of glycosaminoglycans and particularly of hyaluronic acid and dermatan sulfate to their corresponding oligo- and or monosaccharides is of particular value for this purpose for both topical and internal administration. Thus the present invention contemplates use with the following: hyaluronidase; iduronidases such as $\alpha$-L- or exo-hydrolase-$\alpha$-L-iduronidase; aminidases such as N-acetylglucosaminidase or endo-N-acetylhexosaminidase; glucuronidases such as endo-$\beta$-glucuronidase; sulfatases such as iduronate-2-sulfatase and N-acetylglucosamine 6-sulfatase; and other enzymes involved in the catabolism of glycosaminoglycan structural polymers of the body.

The formulations may be further enhanced by use with a redox reagent. As defined here, redox reagents are compounds which can readily accept (be reduced by) or donate (thereby become oxidized) an electron. Such reagents are particularly useful when the reaction is reversible, but the invention is not so limited. Without being bound by theory, it is is believed that redox reagents in this use serve as a reservoir or catalyst for the rapid transfer of charge during the cleavage step. Nontoxic organic redox reagents are particularly of value, and for instance include: flavoenzymes and their coenzymes; anthracene-based compounds such as anthraquinone, alizarin, and related natural dyes; nonbenzenoid aromatic compounds such as azulene and its natural derivatives such as chamazulene; and other semiconductive conjugated compounds such as carotene and lycopene.

The rate of degradation in the present invention may be enhanced by irradiation increase the energy level of the enzyme substrate. This includes, for instance, the use of low-level infrared radiation from a lamp or more preferably an optical fiber, during administration to raise the temperature at the degraded portion of the body by ca. 5-10° C. With optical fiber this can be employed in internal applications. In an alternative embodiment ultraviolet irradiation is used in combination with semiconductive organic compounds during topical administration; without being bound by theory it is believed that the organic compounds provide a safe and efficient energy transfer mechanism for the light. Again, lamps and optical fibers are appropriate for use. In a different embodiment ultrasound is applied to the treatment site during administration. Such sonication provides transient high energy at bubbles and pinpoint sites for very short times, avoiding physiological damage; methods to control the location of and the energy levels imparted by sonication are well known in the art.

Non-limiting examples of suitable compositions include the following: (i) the combination of papain with urea; (ii) the combination of proteinase K with urea, sodium dodecyl sulfate or ethylenediaminetetraacetic acid (EDTA); and (iii) the combination of porcine trypsin that has been modified by reductive methylation, with 0.1% sodium dodecyl sulfate, 10% acetonitrile or 2M guanidine hydrochloride.

The composition may contain more than one debridement enzyme. One of these enzymes may be papain. Papain is active over a pH range of 3 to 12. Moreover, unlike some proteases, papain is not inhibited by penicillin or sulfonamide drugs.

In another particular embodiment, the composition includes (i) more than one debridement enzyme, wherein one of the two or more debridement enzymes is papain; and (ii) urea.

The compositions of the present invention may optionally include one or more cofactors to enhance the activity of the debridement enzyme. Nonlimiting examples of cofactors include ATP, ADP, NAD, NADH, NADP, NADPH, oxidized and reduced flavins, folic acid and its derivatives, and other cofactors that are familiar to those of ordinary skill in the art. Contemplated concentrations for these cofactors include stoichiometric ratios from 0.1 to 10.0 moles of the cofactor per mole of debridement enzyme, more particularly the range of 0.3 to 3.0 moles of the cofactor per mole of debridement enzyme, and still more particularly about 1.0 mole of the cofactor per mole of debridement enzyme. Depending on the diffusion rate, reactive rate and biodegradability of a cofactor relative to that of the enzyme, it may be preferable to employ either more or less than the stoichiometric ratio of the enzyme-cofactor complex or enzyme-cofactor reactive sequence that is present during the catalytic events.

In one embodiment, the present invention is a composition useful for the treatment of cancer and other disorders of abnormal cell proliferation which includes (i) one or more debridement enzymes; and (ii) a denaturant, wherein the debridement enzyme is not papain.

In a particular embodiment, the debridement enzyme is selected from the group consisting of plasma enzymes, pancreatic enzymes, cysteine proteases, serine proteases and metallopeptidases, and optionally, fibrinolysin, desoxyribonuclease, trypsin, chymotrypsin, krillase, bromelain, ficin, subtilisins, proteinase K, collagenases, vibriolysin, thermolysin, streptokinase, streptodornase, and proteolytic enzymes excreted by maggots.

In another embodiment, the present invention is a composition useful for the treatment of cancer and other disorders of abnormal cell proliferation, which includes (i) papain; and (ii) a denaturant selected from the group consisting of I$^-$, ClO4$^-$, or SCN$^-$; a salt or base in which the cation is Li$^+$, Mg$^{++}$, Ca$^{++}$, Ba$^{++}$, or guanidinium; lactic acid; citric acid; an aliphatic alcohol; 13-mercaptoethanol; a detergent; sodium dodecyl sulfate; formaldehyde; acetone; acetonitrile; dimethylsulfoxide; dimethylformamide; propylene carbonate; ethylene carbonate; a drug containing a heavy metal; a drug containing silver; a drug containing mercury; a drug containing lead; silver sulfadiazine; gentamicin; penicillin; metal scavengers;

strong acids, strong bases, and heat such as the application of infrared heat to a lesion during treatment.

Pharmaceutical Formulations and Administration

A subject, such as human or other mammal, suffering from a disorder of abnormal cell proliferation can be treated by administering to the affected area an effective amount of the composition of the present invention. The composition can be administered to a subject as a pharmaceutical composition, i.e., including a pharmaceutically acceptable carrier.

As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical formulation may also include a pharmaceutically acceptable prodrug or salt of the debridement enzyme and or denaturant in the presence of a pharmaceutically acceptable carrier or diluent. Non-limiting examples of enzyme prodrugs include, for instance, derivatives comprising acetyl esters of the hydroxyl groups on the enzyme. Non-limiting examples of salts of a debridement enzyme include, for instance, derivatives comprising sodium or potassium salts of the carboxylic acid group. The active materials can be administered by any route that is suitable for treating the disorder, for example, by cannulus, parenterally, orally, or intravenously, in liquid or solid form.

The concentration of the debridement enzyme in the pharmaceutical composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Non-limiting, suitable doses for the debridement enzyme include from about $1\times10^4$ to $1\times10^8$ USP per gram, more particularly from about $1\times10^5$ to $1\times10^7$ USP per gram, still more particularly from about $5\times10^5$ to $5\times10^6$ USP per gram, and yet more particularly about $1.1\times10^6$ USP per gram.

A particularly useful activity range of the debridement enzyme for an internal cancerous lesion is in the range from about $1\times10^5$ to $5\times10^6$ USP, for example for papain.

The effective dosage can be estimated, for instance, based upon the activity of the enzyme, the mass of tissue to be eliminated in each iteration of treatment, and with some consideration to the control of the amount and distribution of compounds released from the dying cells.

Where one or more layers of cells are to be removed from the perimeter of a lesion over a treatment iteration lasting for a period of five minutes or longer, approximately 0.5 mL of formulation per $cm^2$ of the lesion surface treated may suffice.

The particular range for denaturant will depend upon the choice of denaturant.

In a particular embodiment of the composition, the denaturant is present from about 0.1 to about 40 weight percent of the composition; more particularly in the range of from about 2 to about 30 weight percent; still more particularly from about 5 to about 20 weight percent; yet more particularly from about 7 to about 15 weight percent; even more particularly over about 10 weight percent; over about 15 weight percent; and from about 1-5 weight percent.

In a more particular embodiment, wherein papain is present, from about 7-15 weight percent of urea is employed, e.g., 10 weight percent, however other denaturants may be effective in smaller amounts, thus approximately 0.1% sodium dodecyl sulfate may be used in combination with porcine trypsin that has been modified by reductive methylation.

Where heat is used as a denaturant or to assist denaturation by chemical means the heat may be conveniently applied as a focused beam (e.g., infrared through an optical fiber) at a rate and duration predetermined empirically to achieve the desired temperature.

The activity of enzymes exists on a spectrum that covers orders of magnitude, and may be useful over a substantial range of that spectrum. Thus if a denaturant of choice reacts with the debridement enzyme of choice and leaves just 10% of the native activity of that debridement enzyme, the residual activity may be enough. And in some cases slower-acting formulations such as a 10% active formulation may be desirable, e.g., for the purpose of enhancing the selectivity of destruction or for the purpose of keeping streaming fluids from dead or dying cells at a medically manageable level. Of course from the perspective of cell destruction, a complete absence of denaturation of the debridement enzyme provides the most efficient and cost-effective results.

Biochemical vendors commonly supply enzymes in a medium that contains an enzyme stabilizing compound such as glucose, lactose or other stabilizing compound. The stabilizer can enhance the activity of the enzyme during debridement, for instance it has been found in the present discovery that papain formulated without a stabilizer such as lactose is only 50-60% as effective in cell removal from lesions as papain formulated with a stabilizing quantity of lactose. The pharmaceutical compositions disclosed herein for treatment of abnormal cellular proliferation are formulated at any convenient concentration of these stabilizing compounds that leaves significant activity of the debridement enzyme. For instance the cancer-treating formulation disclosed herein may comprise typical intravenous concentrations of lactose or glucose, or may have the same concentration of stabilizer that was present when the enzyme was obtained as a starting material from the supplier, or may contain only the amount of stabilizer that was present in the enzyme media obtained from the vendor.

In a particular embodiment, the composition may contain up to 50 weight percent of stabilizing compound.

The method of administration used in the present invention may vary and include any suitable mode of administration. The mode of administration may vary depending upon the patient and the particular cancer or other disorder at issue, as would be understood by one skilled in the area. Non-limiting examples of suitable modes of administration according to the present invention include parenteral, intravenous, intradermal, subcutaneous, oral, inhalation, transdermal, topical, transmucosal and rectal administration.

The method disclosed herein is not limited by the form of formulation or delivery, and contemplates the use of liquids, intravenous solutions, isotonic solutions, solids, creams, sprays, hydrophilic ointments, emulsions, suppositories, controlled release formulation, swab applicators, and other pharmaceutical formats such as are known to those in the art.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The mixtures disclosed herein can also be mixed with other active materials that do not impair the desired action, or with materials that supplement the desired action, such as antibiotics, antifungals, anti-inflammatories, or other antivirals, including other nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the mixture disclosed herein is prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

For example, the debridement enzyme and the denaturant may be embedded in a biodegradable surgical dressing that is applied to the tissue surrounding a cancerous lesion, where that lesion has been surgically removed entirely or in part.

Non-limiting illustrative formulations include the following specific embodiments. The excipients of these embodiments enhance ancillary properties, for instance, methylparaben is a preservative; edetate disodium chelates cationic electrolytes; polyoxyl 40 stearate provides viscosity; etc. The selection and combination of excipients to optimize the physical and chemical properties of compositions is familiar to those skilled in the art of pharmaceutical formulation. Note that these embodiments are merely illustrative, for instance, for internal use one could omit fragrance.

Formulation no. 1 (ACCUZYME® ointment, Physician's Desk Reference, 2005) (manufactured by DPT Laboratories Ltd., San Antonio, Tex., and marketed by Healthpoint solutions, Fort Worth, Tex.):
  papain, USP ($8.3 \times 10^5$ USP units of activity per gram)
  urea, USP 10% in a hydrophilic ointment base
  Ointment Base:
  emulsifying wax
  fragrance
  glycerin
  isopropyl palmitate
  lactose
  methylparaben
  potassium phosphate monobasic
  propylparaben
  purified water Formulation no. 2 (ACCUZYME® ointment. Physician's Desk Reference, 2000):
  papain, USP ($1.1 \times 10^6$ USP units of activity per gram)
  urea, USP 10% in a hydrophilic ointment base
  Ointment Base:
  emulsifying wax
  fragrance
  glycerin
  isopropyl palmitate
  lactose
  methylparaben
  potassium phosphate monobasic
  propylparaben
  purified water Formulation no. 3 (ETHEZYME™ 830 ointment generic product):
  papain, USP ($8.3 \times 10^5$ USP units of activity per gram)
  urea, 10% in a hydrophilic ointment base
  emulsifying wax
  fragrance
  glycerin
  edetate disodium
  isopropyl palmitate
  methylparaben
  polyoxyl 40 stearate
  potassium phosphate monobasic
  propylparaben
  mixed tocopherols
  purified water Formulation no. 4 (PANAFIL™ Healing, Debriding & Deodorizing Ointment):
  standardized papain, USP ($\geq 4.059 \times 10^5$ USP units of activity per gram of ointment),
    urea USP 10% and
    chlorophyllin copper complex sodium 0.5%
    in a hydrophilic base composed of Purified Water, USP;
    propylene glycol, USP;
    white petrolatum, USP;
    stearyl alcohol, NF;
    polyoxyl 40 stearate, NF;
    sorbitan monostearate, NF;
    boric acid, NP;
    chlorobutanol (anhydrous), NF as a preservative;
    sodium borate, NF.

Without being bound by theory, the papain-and-urea ointment and spray products produced commercially are believed to leverage two chemical actions: (1) the urea exposes by solvent action the activator groups of papain, thereby increasing its efficacy; and (2) the urea denatures the nonviable protein matter in lesions and thereby renders it more susceptible to enzymatic digestion. Pharmacologic studies have shown that the combination of papain and urea result in twice as much digestive activity as papain alone.

Use of debridement enzymes for cancer therapy is not limited to topical creams or sprays; it may be taken internally, particularly where the enzymes and other compounds selected are known to have low toxicity. For instance, bromelain is a component of pineapple stems. The natural denaturant urea is safe for human consumption in modest quantities, in fact it has been used as a medicinal compound, being administered to humans as a diuretic at dosages as high as 60 g per day. Experiments with repeated ingestion of ⅛ teaspoon ACCUZYME® by an adult male patient have observed no negative effects other than a slight bitter taste. Also, because the papain retains its enzymatic activity between pH 3 and pH 12, it will retain its pharmacological benefits in a variety of physiological conditions. The amount of enzymatic activity in a dose can be controlled by methods that are well known in the art. The level of catalytic activity stated for debridement enzymes herein and in the art is in units per gram, thus the number of grams used determines the dosage. Typical formulations have densities of ca. 1 g/ml, thus the volume and extent of further dilution can also be used to control the administered dosage. For instance, if medication having an activity level of $1.1 \times 10^6$ enzymatic activity units (per gram) is diluted by a factor of 10, then 3 ml of the diluted formulation is [3 ml*(1 g/ml)*($1.1 \times 10^6$ activity units/g)]/10=$3.3 \times 10^5$ unit dosage.

In dosage and administration, the area to be treated is preferably cleansed before administration of the ointment. Example cleansing solutions include ALLCLENZ® Wound Cleanser (manufactured by DPT Laboratories Ltd. of San Antonio, Tex.; marketed by Healthpoint, Ltd., 3909 Hulen Street, Fort Worth, Tex. 76107, phone: (800) 441-8227) or saline solution. Cleansing with hydrogen peroxide may inactivate the papain, thus oxidizers such as hydrogen peroxide are to be avoided to the extent that they would substantially inactivate the papain. The ointment may be applied directly to the treatment area, which may then be optionally covered with an appropriate dressing secured into place. A particularly useful frequency for the ointment application is once or twice daily, though the application may be more or less frequent. It is a particularly helpful practice to irrigate the treatment area at each redressing to remove any accumulation of liquefied necrotic material. Note that papain may be inactivated by contact with salts of heavy metals such as lead, silver and mercury, thus during treatment with papain ointment it is also preferred to avoid contact of the treatment area with medications that contain heavy metals to the extent that they would substantially inactivate it.

In a particular embodiment, the method involves administration by the following steps: (i) a large bore needle containing a cannula is placed to or through the patient's lesion, optionally with the aid of ultrasound images of the body; (ii) the cannula is withdrawn from the large bore needle; (iii) a guide wire is threaded through the needle and placed at the target, optionally with the aid of ultrasound images of the body; (iv) a dilator is used to dilate the tract over the guide wire to the patient's lesion; (v) a catheter that is optionally curved at one end is placed at the target, secured to the body, and left in place; (vi) at least one of the debridement enzyme and the denaturant is administered to the cancerous lesion through the catheter; (vii) optionally the treated cells are irrigated through the catheter and the exudate from the dissolution of cancer cells is suctioned out through the catheter by a syringe.

A cancerocidal formulation can be applied directly internally by the following techniques. An exemplary catheterization methodology is already in use by interventional radiologists to drain fluid collections from various parts of the body including breasts:
  (a) a large bore (e.g., #11 or #14 or 21-gauge) needle with a cannula is placed using ultrasound-guidance either to or through the patient's lesion, preferably at the center;
  (b) the cannula is withdrawn and a guidewire (e.g., a 0.038" guidewire, an 0.018" extra-stiff guidewire with platinum tip or an 0.18" kink-resistant guidewire) is then placed at the targets through the large bore needle, also using ultrasound as a guide;
  (c) a dilator is then used to dilate the tract over the guidewire to the patient's lesion; and
  (d) a catheter preferably with a curve at the end is then placed at the target and secured to the breast and left in place; this catheter can then be used for the insertion of any material that is needed as well as irrigated (for example the debridement enzyme and or an irrigant can be injected through the catheter by means of a 50 cc sterile plastic syringe);
  (e) the exudate from the dissolution of cancer cells is also suctioned out by a syringe through the catheter;
  (f) the alternating injection and suctioning are repeated as necessary; and
  (g) at the end of the course of therapy the catheter is withdrawn.

Needle introduction methods commonly used in biopsies can facilitate injection and aspiration for the methods disclosed herein. Both needle biopsies and core biopsies often contain the following hardware: an introducer needle for positioning a second needle that will be inserted more deeply; the second needle (the one used for actual biopsy); a detachable locking hub to enable rapid changing of peripheral attachments on external end of the more deeply inserted needle; and attachments such as a syringe barrel. Adoption of methods employed in core biopsies will be particularly convenient for the methods disclosed herein where a substantial amount of material needs to be injected or aspirated, or where several serial injection and or suction steps will be needed. Moreover the use of biopsy hardware for injection of debridement compositions and for suction of fluids following treatment also enables convenient periodic sampling of tissue to monitor the progress of internal debridement therapy.

A core biopsy allows a physician to obtain a sample that is significantly larger than that obtained with an aspiration needle set. In addition, an automated core biopsy set promotes more rapid attainment of sequential tissue samples with less damage to the tissue or discomfort to the patient. Design characteristics of an automated biopsy system should interact to improve clinical results during each step of the procedure. Thus adapting the appropriate protocols of a core biopsy for the present method, in one embodiment first an introducer needle is positioned at the site for entry of the needle for transferring debridement compositions. A low profile introducer needle facilitates safer coaxial access. A laser-etched cannula provides visual confirmation of depth of penetration, and an echogenic cannula tip enhances sonographic imaging. The debridement transfer needle is then introduced through the cannula until the handle is flush with the hub. Sequential cutting by the stylet and cannula enables serial treatment at progressive points in a lesion. Single-handed operation is possible when a thumb action controls cocking, firing and sample retrieval. A precision-ground, electropolished stylet and cutting-cannula provide the sharpness required to obtain a clean, uncrushed specimen. A delta-cut needle makes it possible to cut larger deposition troughs in a lesion or to take large biopsy samples by providing a 40% larger cross-sectional surface area than traditional needles, and 43-64% increase in sample weight. Repositioning of the cannula can allow subsequent injections to be made or subsequent samples to be obtained. Alternatively, a detachable biopsy system can be used to obtain multiple samples.

A detachable hub on a biopsy system is designed to allow a physician to acquire multiple biopsies with a single puncture. A tapered throat funnels a stylet into a cannula more smoothly. A locking mechanism can be designed to allow rapid cannula attachment and removal. A channel-cut needle is designed to hold a biopsy sample securely within the biopsy notch for sample retention. In addition, a channel-cut needle provides a larger cross-sectional surface area than traditional needles and a 29-36% increase in sample weight. The detachable hub used in combination with the present method allows rapid swapping of syringe barrels to alternate between debriding injection, irrigation, suctioning, and tissue sampling.

Where debridement of smaller volumes is warranted or where only one or a few administrations are contemplated, it may be more convenient to employ the hardware and relevant methods of needle biopsies. In evaluating a device for fine needle aspiration biopsy, device characteristics such as stylet design need to be evaluated on the basis of how they interact during each step of a procedure to achieve the desired clinical result. In one embodiment, after local anesthesia procedure, the skin is punctured and the needle advanced through the subcutaneous tissue to the target site. The needle must be kept perpendicular to the skin during insertion. During this step, the conical tapered stiletto point of the needle is designed to permit the achievement of a traumatic localization to the lesion. Once at the site, keeping the needle perpendicular to the skin surface, the syringe should be aspirated. During this step, a syringe plunger that locks automatically is designed to permit one-handed use of the device. The needle should be advanced to the appropriate depth rapidly (one full second), keeping the syringe in aspiration. A surgically sharp cutting edge on the needle allows for cleaner, higher quality samples and internal surfaces, compared to other manual devices, enabling rapid debridement with a minimum of scar tissue. A taper on the stylet provides direct contact with the lumen of the barrel. Such direct contact enhances suction within the needle, allowing aspiration of fluids and also allowing a biopsy sample to be withdrawn if desired. Upon completion of the procedure the needle is withdrawn completely, the syringe-plunger locking device is unlocked, and the biopsied specimen is removed from the needle lumen by pushing the plunger while the needle is aimed directly into the specimen bottle. Thin-walled construction of a needle improves specimen weight for the gauge size available.

A biopsy needle set should also meet additional criteria for an aspiration biopsy: usable in a broad range of procedural applications including the liver, kidney, prostate, breast, thyroid, pancreas, spleen and lung; and allows flexibility of imaging modality in CT, fluoroscope and ultrasound.

During non-vascular procedures, a well-designed introducer system provides for more accurate placement of an 0.038" guidewire. As always, design characteristics are closely related to clinical performance for any introducer system. During introduction, a 21-gauge diagnostic needle may reduce tissue trauma. An 0.018" extra-stiff guidewire with platinum tip offers excellent visibility; an alternative to allow for physician preference is an 0.018" kink-resistant nitinol guidewire. A coaxial dilator/sheath assembly designed with a locking stiffening cannula promotes stable over-the-wire placement. A proximal taper on the dilator/sheath assembly eases introduction and placement, while a radiopaque marker at the tip of the sheath can enhance visualization for more precise placement. A reference mark is designed to permit more accurate alignment of sheath and dilator tips for wire placement. A large sheath end-hole inner diameter allows placement of an 0.038" working guidewire while an 0.018" guidewire remains in place as safety wire. An 0.038" heavy-duty guidewire that is available with either a "J" tip or a straight tip allows a physician to choose the configuration best suited to the patient and provides excellent performance as a working wire.

In some clinical areas, biopsy systems and introducer designs are undergoing constant change, while in others, designs are well established and unlikely to change significantly in the short- or even long-term. But both for biopsies and for internal debridement, the choice of hardware and methods will be guided by the clinical advantage of each component of the device, as well as the overall effect of the interaction among the various elements, in order to select a device that will achieve desired clinical results.

Appropriate guides and catheters are also in common use for purposes such as to drain lesions, e.g., a breast abscess. These and comparable or analogous catheters and guidewires and co-axial needles can be used for the purposes of the methods disclosed herein. The magnitude of the inner diameter of the catheter chosen will depend on the size of the tumor, up to ⅛ inch for substantial tumors and up to ¼ inch for a large cancer in the human body. It is convenient to employ a catheter inside of which is a stylet with a sharp end protruding from the insertion end of the catheter; the stylet's protruding sharp end penetrates an organ, or for instance penetrates a breast, thus assisting the insertion of the catheter, after which the stylet is withdrawn and the catheter is left in place to deliver medication and irrigation to the lesion, and to aspirate fluids that collect following treatment.

Suitable equipment is available from the following manufacturers: InterV Medical Devise Technologies, Inc., 3600 S.W. 4th Ave., Gainesville, Fla. 32608 (352) 338-0440; Boston Scientific, 480 Pleasant St., Watertown, Mass. 02472 (800) 225-3226; and Cook Inc., 750 Daniels Way, P.O. Box 489, Bloomington, Ind. 47412 (812) 339-2235 and (800) 457-4500. Thus, for instance, a catheter attached to a 50 cc sterile syringe can be used to administer debridement enzyme to a breast carcinoma by insertion of the catheter into the breast, pancreas carcinoma by insertion of the catheter into the abdomen, or carcinomas of internal organs or the brain by analogous insertions. For example a biopsy needle set from Boston Scientific can be used, Or for example Quick-Core® biopsy needles, optionally coaxial and currently available from Cook Inc. can be used, which have a plunger, a cutting cannula, a throw length of 10 mm or 20 mm, with a specimen notch and inner stylet.

The topical or internal cancerous area may be treated in advance of the papain treatment with a wound cleanser such as ALLCLENZ® Wound Cleanser (sold by Healthpoint, Ltd., Fort Worth, Tex., manufactured by DPT Laboratories, Ltd, San Antonio, Tex.) or saline. Cleansing with hydrogen peroxide may be counterproductive as it may inactivate the papain. Use of salts of medications containing heavy metals such as lead, silver and mercury may also be counterproductive as they may inactive the papain. A papain-based ointment may be applied directly to the cancerous area, covered with an appropriate dressing and secured in place. Daily or twice daily applications are preferred. The cancerous area is preferably irrigated at each redressing to remove any accumulation of liquified necrotic material.

The invention will now be described in greater detail by reference to the following non-limiting examples.

EXAMPLES

Example 1

BT-20 human breast carcinoma cells were grown to confluency in 60 mm diameter cell culture dishes. Each dish contained approximately 3 million cells. Three treatment groups were established:
 the control group with no application of the cream;
 the first test group with an application of ACCUZYME® ointment by a pipette tip; and
 the second test group with an application of ETHEZYME™ 830 papain/urea cream by a pipette tip.

Cream was applied to the treatment groups at multiple points on the cell culture dish. Cells were observed by microscopic examination for morphological changes. At 15 minutes after application of the cream, cells near the site of application were observed to begin detaching from the cell culture dish. At the margins of the cream application, cells began to change shape by rounding up, shrinking, and losing their fibroblast-like appearance. Cells closest to the margin of cream application showed the most profound changes, with morphological changes that diminished in magnitude with their distance from the original application site of the cream. Many of the areas closest to the cream became cell free due to substantial cell detachment. During this time course, no morphological changes were noted in the control group that did not receive any cream application. A more striking response for cell rounding and detachment was noted for the ACCUZYME® ointment as compared to the cell response to the ETHEZYME™ 830 papain/urea cream. At one hour, cells in the control group began to detach due to lack of serum and the experiment was stopped.

The ACCUZYME® enzymatic debriding ointment as labeled contained papain, USP ($6.5 \times 10^5$ USP units of activity based on Lot 10C389 per gram of ointment) and urea, USP 10% in a hydrophilic ointment base composed of emulsifying wax, fragrance, glycerin, isopropyl palmitate, lactose, methylparaben, potassium phosphate monobasic, propylparaben, and purified water.

The cream was highly effective at all ACCUZYME® concentrations tested in this study: $1.1 \times 10^6$ USP units of activity (PDR 2000); $8.3 \times 10^5$ USP units of activity (PDR 2005); and $6.5 \times 10^5$ USP units of activity; where the PDR notation refers to the Physician's Desk Reference and its year of publication for the stated concentration amount under the respective Healthpoint products entries. In this Example, dilutions below $1.1 \times 10^6$ USP units of activity were made using saline solution as the dilutant. In a preferred range the papain-based ointments such as those used in this Example are employed at a concentration up to about $10^8$ USP units of activity, more preferably at a concentration up to about $10^7$ USP units of activity, more preferably in a range of $1 \times 10^5$ to $3 \times 10^6$ USP units of activity, still more preferably in a range of $6 \times 10^5$ to $2 \times 10^6$ USP units of activity, and still more preferably at a concentration of $1.1 \times 10^6$ USP units of activity.

Example 2

A cancerocidal formulation is applied directly to a breast carcinoma for as many as fourteen consecutive days or more by the following techniques. These catheterization methodologies are already in use by interventional radiologists to drain fluid collections from various parts of the body including breasts.

A large bore (e.g., #11 or #14 or 21-gauge) needle with a cannula is placed using ultrasound-guidance either to or through the patient's lesion, preferably at the center.

The cannula is withdrawn and a guidewire (e.g., a 0.038" guidewire, an 0.018" extra-stiff guidewire with platinum tip or an 0.18" kink-resistant guidewire) is then placed at the targets through the large bore needle, also using ultrasound as a guide.

A dilator is then used to dilate the tract over the guidewire to the patient's lesion.

A catheter preferably with a curve at the end is then placed at the target and secured to the breast and left in place. This catheter can then be used for the insertion of any material that is needed as well as irrigated. For example the debridement enzyme and or an irrigant can be injected through the catheter by means of a 50 cc sterile plastic syringe. The exudate from the dissolution of cancer cells is also suctioned out by a syringe through the catheter. This is done on a daily or twice daily basis. When therapy is complete the catheter is withdrawn.

The area to be treated may be treated in advance of the papain treatment with a wound cleanser such as ALLCLENZ® Wound Cleanser (sold by Healthpoint, Ltd., Fort Worth, Tex., manufactured by DPT Laboratories, Ltd, San Antonio, Tex.) or saline. Cleansing with hydrogen peroxide may be counterproductive as it may inactivate the papain. Use of salts of medications containing heavy metals such as lead, silver and mercury may also be counterproductive as they may inactive the papain. A papain-based ointment may be applied directly to the cancerous area, covered with an appropriate dressing and secured in place. Daily or twice daily applications are preferred. The cancerous area is preferably irrigated at each redressing to remove any accumulation of liquified necrotic material.

Example 3

A patient with a history of basal skin cell cancer on the forehead, removed by wide excision, subsequently developed solar and actinic keratosis on the forehead and cheeks. The patient's new lesions were treated with PANAFIL-TX®, a papain/urea product containing chlorophyllin. The numerous skin lesions turned dark red after treatment, and then the patient's complexion cleared completely. Reaction with the lesions was very fast, showing results within 15 minutes of application to the lesions. The PANAFIL-TX® contained chlorophyll, which temporarily imparted some green coloration to the treated areas.

Example 4

A patient developed a lesion on the upper left back, which continued to grow over a period of more than two years, reaching a diameter of one half inch and extending deep into the tissue of the back. The lesion did not respond to treatment with cortisone cream, and was diagnosed by shave biopsy as a small superficial multicentric-type basal cell carcinoma. Microscopic examination revealed that the carcinoma was characterized by small aggregates of basaloid cells with peripheral palisading and focal retraction artifact. The tumor aggregates arose from multiple separate sites along the lower epidermis and extended into the papillary dermis. Within the surrounding dermis there was a dense perivascular and interstitial lymphocyte infiltrate. Sections showed the skin with very mild acanthosis, hyperkeratosis, and follicular plugging. Visually the tumor manifested a red lesion with bluish skin on the bottom of the lesion. The lesion was then treated with ACCUZYME® papain/urea product. The lesion responded to treatment over a period of one to three days, but a 10-day course of treatment was followed. The patient felt a slight burning sensation, but no Tylenol® or other pain medication was needed. Normal cells neighboring the lesion were not compromised by the treatment, and about five weeks after the patient had begun treatment with a papain-urea product another shave biopsy yielded a negative finding for basal cell carcinoma. Acanthosis, hyperkeratosis, and hypergranulosis with dermal eosinophils were observed in the second biopsy; within the dermis there was fibrosis and a sparse infiltrate of lymphocites and eosinophils.

Example 5

A patient was diagnosed by shave biopsy as having a small inflamed superficial basal cell carcinoma on the lower back/bottom. Microscopic examination revealed that the carcinoma was characterized by aggregates of basaloid cells with peripheral palisading and focal retraction artifact. There was a dense perivascular and interstitial infiltrate of lymphocytes and numerous eosinophils within the dermis. Scattered eosinophils were also present within the adjacent epidermis associated with spongiosis. Upon treatment with ACCUZYME® for 10 days as in Example 4 the carcinoma was eliminated.

Example 6

A colloidal intravenous solution is made which comprises sterile water or a dilute saline solution to deliver a dose in the range of $1.3 \times 10^5$ USP papain to $1.1 \times 10^6$ USP papain depending on the size of the patient, and 100 mg urea USP per gram of papain. A normal pediatric dose is about $4.3 \times 10^5$ USP papain, and 100 mg urea USP per gram of papain. The solution is delivered by cannulus or other intravenous means to treat a carcinoma, colon lesion, or general cancer in an animal or human. Excised cells from the cancer to be treated are first assayed in a cell culture tray to confirm the optimal dose of papain formulation to be delivered.

Example 7

ACCUZYME® is applied to the interior of a breast cancer in an adult female human, infiltrating ductal carcinoma, by the catheterization method of Example 2, with aspiration of the streaming fluid from the dying cancer cells through a cannulus, the end of which is placed just below the lesion. The patient is treated with TYLENOL® or TYLENOL #3™ every six hours to alleviate any discomfort experienced from the treatment. To prevent infection during treatment the patient is started on a regimen of 500 mg KEFLEX® twice a day for ten days while treatment is under way.

Example 8

ACCUZYME® is applied to a cancer of the pancreas, liver or gall bladder in an adult human by catheterization through the abdomen to the corresponding organ in a manner analogous to Example 2. The patient is treated with CIPRO® 500 mg by mouth every 12 hours or LEVAQUIN® 500 mg daily for ten days to prevent infection while treatment is under way.

Example 9

A formulation from Example 1 is encapsulated in 24-hour, 48-hour, and 72-hour time-release gel capsules, respectively. The 24-hour capsules are administered to a patient with a cancer in the ascending colon. The 48-hour capsules are administered to a patient with a cancer in the transfer colon. The 72-hour capsules are administered to a patient with a cancer in the descending colon. The capsules are administered at a rate of one to eight capsules per day, destroying the cancer cells while leaving the normal cells intact. The effective dose for each cancer is preferably ascertained in advance by cell culture studies of excised cells from the cancer.

Example 10

A hydrophilic ointment base containing $1.1 \times 10^6$ USP ficin and urea, USP 10% is administered to a cancerous lesion is applied to a breast cancer in an adult female human, infiltrating ductal carcinoma, by the catheterization method of Example 2. The patient is treated with TYLENOL® or TYLENOL #3® every six hours to alleviate any discomfort experienced from the treatment. To prevent infection during treatment the patient is started on a regimen of 500 mg KEFLEX® twice a day for ten days while treatment is under way.

Example 11

A hydrophilic ointment base containing $1.1 \times 10^6$ USP bromelain and urea, USP 10% is administered to a breast cancer in an adult female human, infiltrating ductal carcinoma, by the catheterization method of Example 2. The patient is treated with TYLENOL® or TYLENOL #3® every six hours to alleviate any discomfort experienced from the treatment. To prevent infection during treatment the patient is started on a regimen of 500 mg KEFLEX® twice a day for ten days while treatment is under way.

Example 12

A 2 mL aliquot of a solution containing 20 mg Proteinase K with specific activity >30 units/mg, 1 mM CaCl2, 20 mM Tris-HCl, 2M urea, 50% glycerol, and with pH 8.0 is cannulated in a therapeutic iteration to treat the interior of a breast cancer lesion 2 cm in diameter. Proteinase K is available from Finnzymes Oy, Keilaranta 16 A 02150 Espoo, Finland, Tel. +358 9 584 121).

Example 13

A 2 mL aliquot of a solution containing 20 mg Proteinase K with specific activity >30 units/mg, 1 mM CaCl2, 20 mM Tris-HCl, 5 mM EDTA, and with pH 7.9 is cannulated in a therapeutic iteration to treat the surface of a breast cancer lesion 2 cm in diameter. Proteinase K is available from Finnzymes Oy, Keilaranta 16 A 02150 Espoo, Finland, Tel. +358 9 584 121).

Example 14

2 mL denaturant aliquot of a solution containing 0.5% sodium dodecyl sulfate, 1 mM $CaCl_2$, 20 mM Tris-HCl, and with pH 7.9 is cannulated in a therapeutic iteration to treat the topmost surface of a breast cancer lesion 2 cm in diameter. After 30 minutes a 2 mL debridement aliquot of a solution containing 20 mg Proteinase K with specific activity >30 units/mg, 1 mM $CaCl_2$, 20 mM Tris-HCl, and with pH 7.9 is cannulated in a therapeutic iteration to same site through a cannula that is parallel and adjacent to the cannula containing the denaturant. Proteinase K is available from Finnzymes Oy, Keilaranta 16 A 02150 Espoo, Finland, Tel. +358 9 584 121). Iterations of the two treatments alternate at 30 minute intervals. Streaming fluid from dead and dying cancer cells is aspirated out through a third cannula, the tip of which is placed below the lesion.

Example 15

A 2 mL aliquot of a solution containing 20 ug sequencing grade porcine trypsin that has been modified by reductive methylation, 1 mM $CaCl_2$, 50 mM Tris-HCl, 0.1% sodium dodecyl sulfate, 50 mM acetic acid and with pH 8.0 is cannulated to treat the surface of a breast cancer lesion 2 cm in diameter. 2 mL aliquots of 0.1% sodium dodecyl sulfate in water are subsequent transmitted to same site on the tumor at intervals of 15 minutes for an hour. The porcine trypsin that has been modified by reductive methylation is available from Promega Corporation, 2800 Woods Hollow Road, Madison, Wis. 53711 USA, phone (608) 274-4330.

Example 16

1M urea in saline solution is administered by drip through a cannula at the rate of 8 mL per hour to a site on the surface of a breast cancer lesion; the treatment persists for 1 hour. Then is administered to the same site 4 mL of a solution containing 40 ug sequencing grade porcine trypsin that has been modified by reductive methylation, 1 mM $CaCl_2$, 50 mM Tris-HCl, 1M urea, 50 mM acetic acid and with pH 8.0 is cannulated. The porcine trypsin that has been modified by reductive methylation is available from Promega Corporation, 2800 Woods Hollow Road, Madison, Wis. 53711 USA, phone (608) 274-4330. Subsequently treatment with the urea solution is resumed. The cancerous lesion is illuminated by means of optical fibers, and the progress of the treatment is monitored visually by means of other optical fibers. The streaming fluids are aspirated from beneath the lesion by means of a cannula. The treatment is repeated as necessary and at a frequency appropriate to the condition of the patient.

Example 17

A 2 mL aliquot of a solution containing 20 ug sequencing grade porcine trypsin that has been modified by reductive methylation, 1 mM $CaCl_2$, 50 mM Tris-HCl, 10% acetonitrile, 50 mM acetic acid and with pH 8.0 is cannulated to treat the surface of a breast cancer lesion 2 cm in diameter. 2 mL aliquots of 10% acetonitrile in water are cannulated to the surface of the tumor at intervals of 15 minutes for an hour. The porcine trypsin that has been modified by reductive methylation is available from Promega Corporation, 2800 Woods Hollow Road, Madison, Wis. 53711 USA, phone (608) 274-4330.

Example 18

A biodegradable wound dressing is impregnated with a medium containing $1.1 \times 10^6$ USP papain, 10% urea, and 5% chlorophyllin. Following surgical removal of a breast cancer, the impregnated dressing is cut into strips, which are placed so as to cover the surface of the patient tissue that bordered the cancerous lesion that was removed. The surgical opening is then reclosed.

Example 19

A patient having a small superficial lesion is treated with 3 ml of a mixture consisting of 5 parts Accuzyme® (at $1.1 \times 10^6$ USP units of activity) and one part of propylene carbonate (PC) in which the PC contains 0.1% by weight of vitamin A. The site is exposed to a heat lamp to raise the temperature at the skin by 5° C. above normal, and the site is monitored to keep the temperature within 1° C. of that point. Three minutes after treatment begins the site is irrigated with distilled water and ALL-CLENZ®, then the treatment is repeated two more times.

Example 20

A patient having a small superficial lesion is treated with 3 ml of a mixture comprising 4 parts Accuzyme® (having an aggregate total of $1.1 \times 10^6$ USP units of activity) and one part of dimethyl sulfoxide (DMSO) in which the DMSO contains hyaluronidase (at $1.0 \times 10^6$ USP units of activity).

Example 21

A patient having a small internal lesion is treated by injection with 3 ml of a mixture consisting of 3 parts Accuzyme® (at $1.1 \times 10^6$ USP units of activity) and one part of dimethyl sulfoxide (DMSO) in which the DMSO contains 0.1% by weight of anthraquinone. The site is exposed to low-level ultraviolet light by means of an optical fiber during treatment. Fluids at the site are aspirated out after five minutes of treatment, the site is washed and irrigated with saline solution, which is also then aspirated out, and the procedure is repeated three more times.

Example 22

In vitro dose response studies for the debridement enzyme formulations in anti-cancer use were carried out on 59 human tumor cell lines representing 9 types of cancer by the methods of the In Vitro Cell Line Screening Project (IVCLSP) of the Developmental Therapeutics Program of the National Cancer Institute and National Institutes of Health. The aim of the studies was to identify and prioritize for further evaluation selective growth inhibition or cell killing of particular tumor cell lines. This type of screen is unique in that the complexity of a 59 cell line dose response produced by a given compound results in a biological response pattern which can be utilized in pattern recognition algorithms. Using these algorithms, it is possible to assign a putative mechanism of action to a test compound, or to determine that the response pattern is unique and not similar to that of any of the standard prototype compounds included in the National Cancer Institute database. In addition, following characterization of various cellular molecular targets in the 59 cell lines, it may be possible to further optimize formulations for a specific molecular target. The cancer types tested and the specific cell lines used are shown in the table at the end of this Example. The testing employed the following protocol.

The human tumor cell lines of the cancer screening panel were grown in RPMI 1640 medium containing 5% fetal bovine serum and 2 mM L-glutamine. For a typical screening experiment, cells were inoculated into 96 well microtiter plates in 100 µL at plating densities ranging from 5,000 to 40,000 cells/well depending on the doubling time of individual cell lines. After cell inoculation, the microtiter plates were incubated at 37° C., 5% $CO_2$, 95% air and 100% relative humidity for 24 h prior to addition of the pharmaceutical formulation.

After 24 h, two plates of each cell line were fixed in situ with TCA, to represent a measurement of the cell population for each cell line at the time of drug addition (Tz). Serial dilutions of the ACCUZYME® formulation were prepared by means common in the art, and the formulation was tested at dosages of $10^{-1.8}$ (i.e., 0.01585), $10^{-0.8}$ (i.e., 0.1585), $10^{0.2}$ (i.e, 1.585), $10^{1.2}$ (i.e., 15.85), and $10^{2.2}$ (i.e., 158.5) micrograms of ACCUZYME® formulation per ml of cell culture medium; this series of concentrations corresponds to a range of approximately 0.013 to 130 USP units of enzymatic activity per ml of cell culture medium.

Following drug addition, the plates were incubated for an additional 48 h at 37° C., 5% CO2, 95% air, and 100% relative humidity. For adherent cells, the assay was terminated by the addition of cold TCA. Cells were fixed in situ by the gentle addition of 50 µl of cold 50% (w/v) TCA (final concentration, 10% TCA) and incubated for 60 minutes at 4° C. The supernatant was discarded, and the plates were washed five times with tap water and air dried. Sulforhodamine B (SRB) solution (100 µl) at 0.4% (w/v) in 1% acetic acid was added to each well, and plates were incubated for 10 minutes at room temperature. After staining, unbound dye was removed by washing five times with 1% acetic acid and the plates were air dried. Bound stain was subsequently solubilized with 10 mM trizma base, and the absorbance was read on an automated plate reader at a wavelength of 515 nm. For suspension cells, the methodology was the same except that the assay was terminated by fixing settled cells at the bottom of the wells by gently adding 50 µl of 80% TCA (final concentration, 16% TCA). Using the seven absorbance measurements [time zero, (Tz), control growth, (C), and test growth in the presence of drug at the five concentration levels (Ti)], the percentage growth was calculated at each of the drug concentrations levels. Percentage growth inhibition was calculated as:

$[(Ti-Tz)/(C-Tz)] \times 100$ for concentrations for which $Ti \geq Tz$ $[(Ti-Tz)/Tz] \times 100$ for concentrations for which $Ti < Tz$.

Three dose response parameters were calculated for each experimental agent. Growth inhibition of 50% (GI50) was calculated from $[(Ti-Tz)/(C-Tz)] \times 100=50$, which was the drug concentration resulting in a 50% reduction in the net protein increase (as measured by SRB staining) in control cells during the drug incubation. The drug concentration resulting in total growth inhibition (TGI) was calculated from Ti=Tz. The LC50 (concentration of drug resulting in a 50% reduction in the measured protein at the end of the drug treatment as compared to that at the beginning) indicating a net loss of cells following treatment was calculated from $[(Ti-Tz)/Tz] \times 100 = -50$. Values were calculated for each of these three parameters if the level of activity is reached; however, if the effect was not reached or is exceeded, the value for that parameter was expressed as greater or less than the maximum or minimum concentration tested.

Publications pertaining to these testing methods include the following: Alley, M. C., et al., "Feasibility of Drug Screening with Panels of Human Tumor Cell Lines Using a Microculture Tetrazolium Assay," *Cancer Research*, 48:589-601 (1988); Grever, M. R., et al., "The National Cancer Institute: Cancer Drug Discovery and Development Program," *Seminars in Oncology*, 19(6):622-638 (1992); Boyd, M. R., and Paull, K. D., "Some Practical Considerations and Applications of the National Cancer Institute In Vitro Anticancer Drug Discovery Screen," *Drug Development Research*, 34:91-109 (1995).

Figure 2:
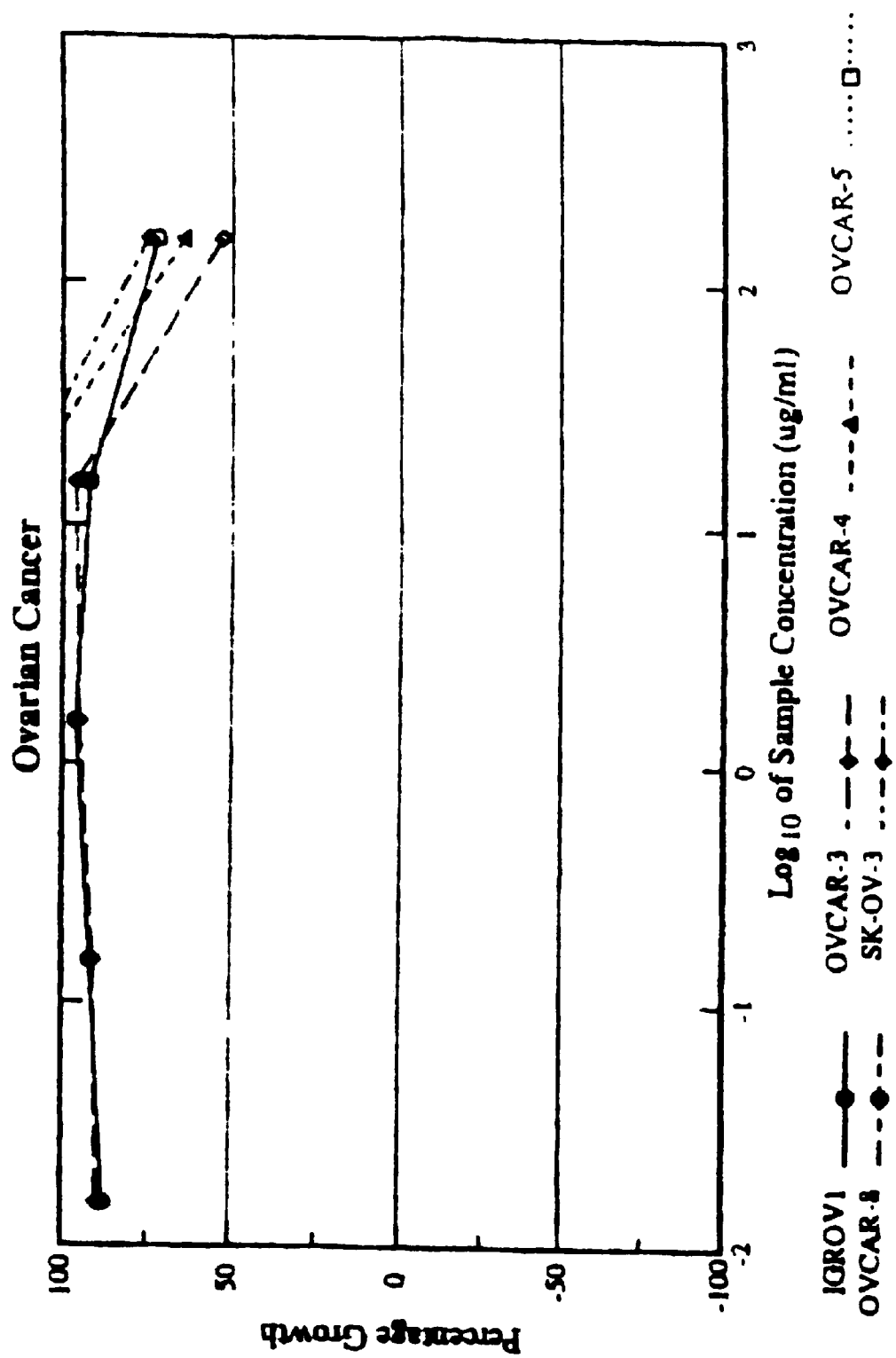
FIG. 2 illustrates the effect of exemplary enzymatic compositions on the growth rate of various ovarian cancer cell lines over a 48 hour period when presented at dilutions representing 0.013, 0.13, 1.30, 13, and 130 USP units of papain enzymatic activity per ml of cell culture medium. These enzymatic activities correspond to papain/urea cream sample concentrations of −1.8, −0.8, 0.2, 1.2 and 2.2 ug/ml.
Figure 3:
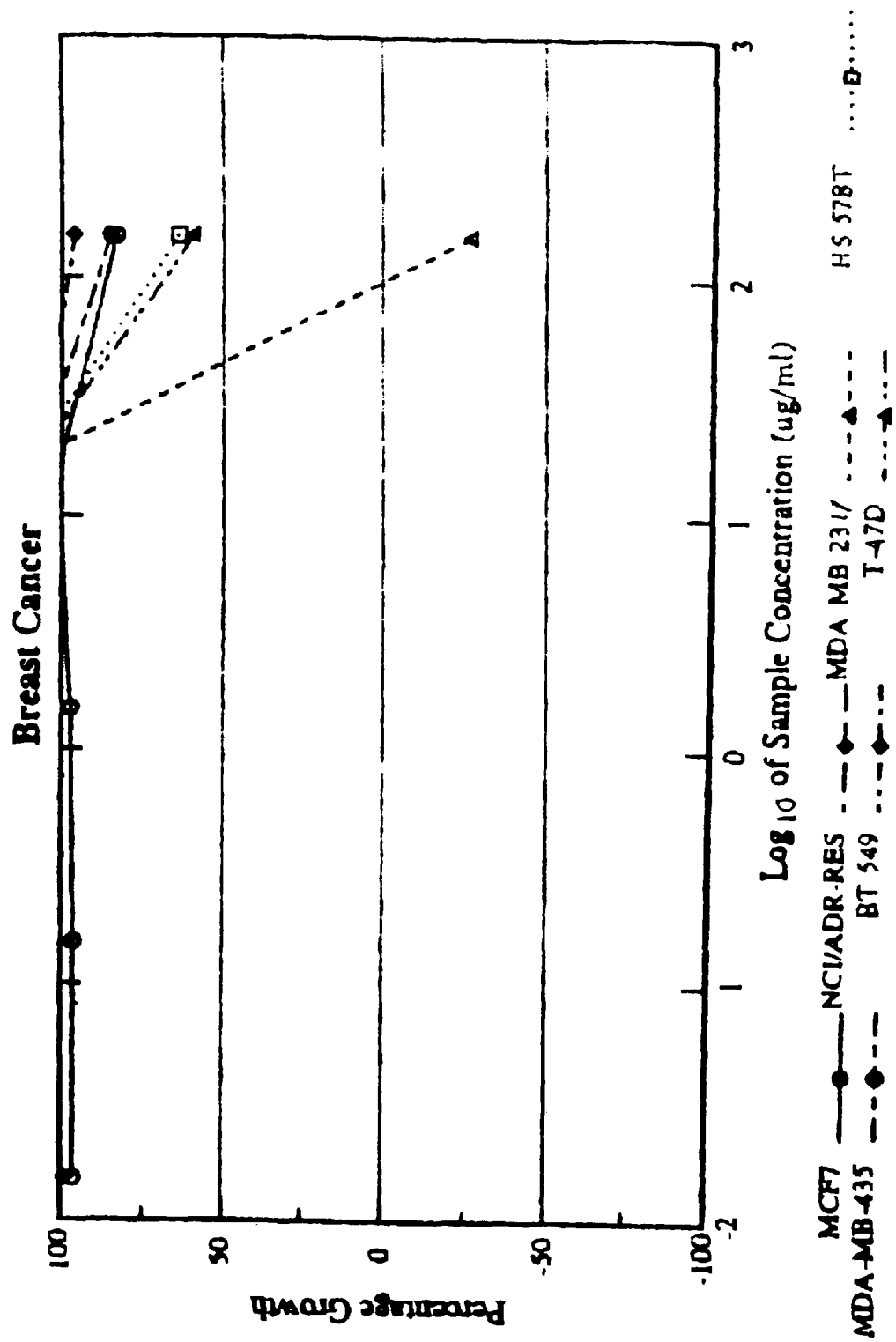
FIG. 3 illustrates the effect of exemplary enzymatic compositions on the growth rate of various breast cancer cell lines over a 48 hour period when presented at dilutions representing 0.013, 0.13, 1.30, 13, and 130 USP units of papain enzymatic activity per ml of cell culture medium. These enzymatic activities correspond to sample papain/urea cream concentrations of −1.8, −0.8, 0.2, 1.2 and 2.2 ug/ml.
Figure 4:
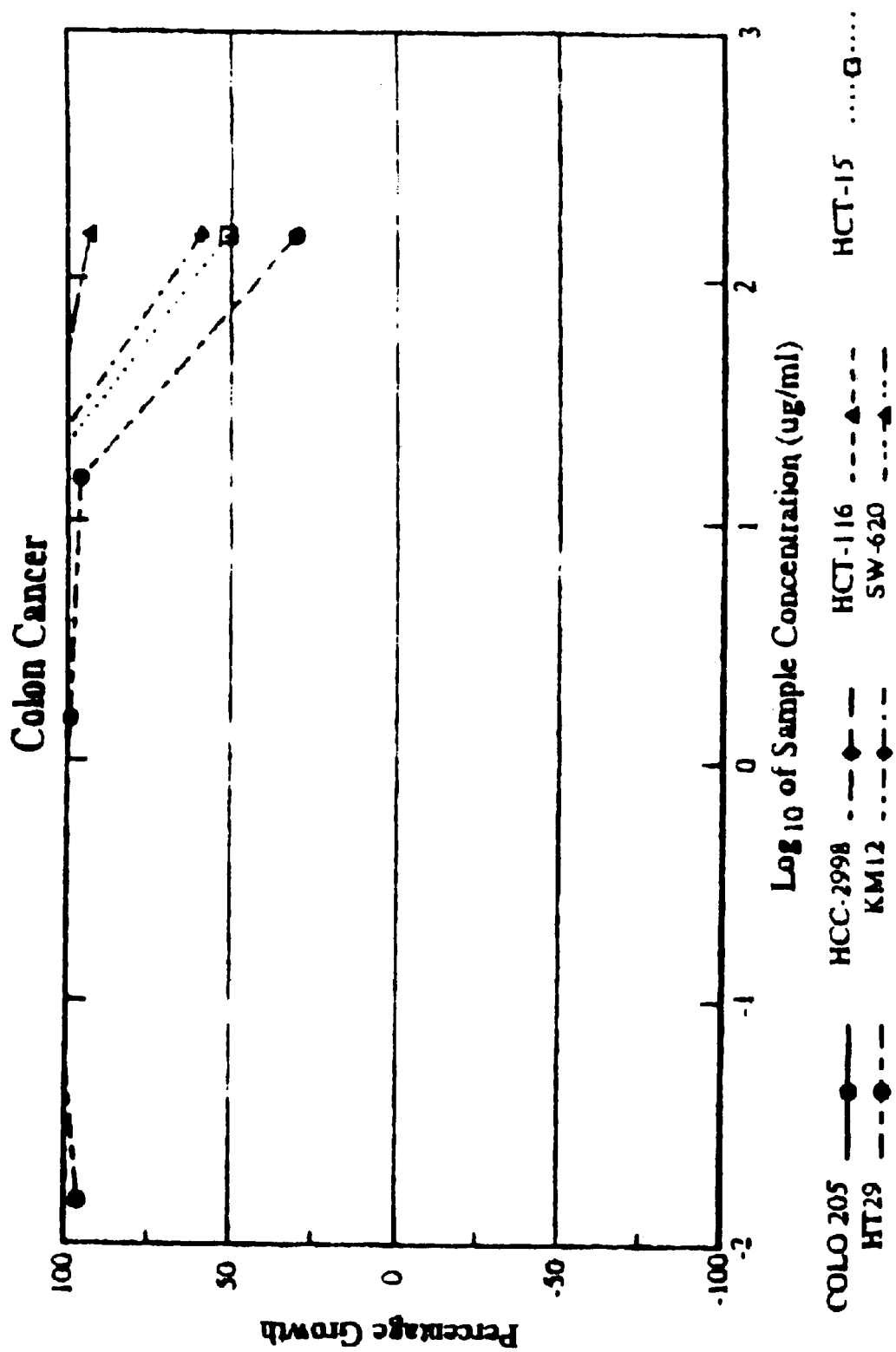
FIG. 4 illustrates the effect of exemplary enzymatic compositions on the growth rate of various colon cancer cell lines over a 48 hour period when presented at dilutions representing 0.013, 0.13, 1.30, 13, and 130 USP units of papain enzymatic activity per ml of cell culture medium. These enzymatic activities correspond to sample papain/urea cream concentrations of −1.8, −0.8, 0.2, 1.2 and 2.2 ug/ml.
Figure 5:
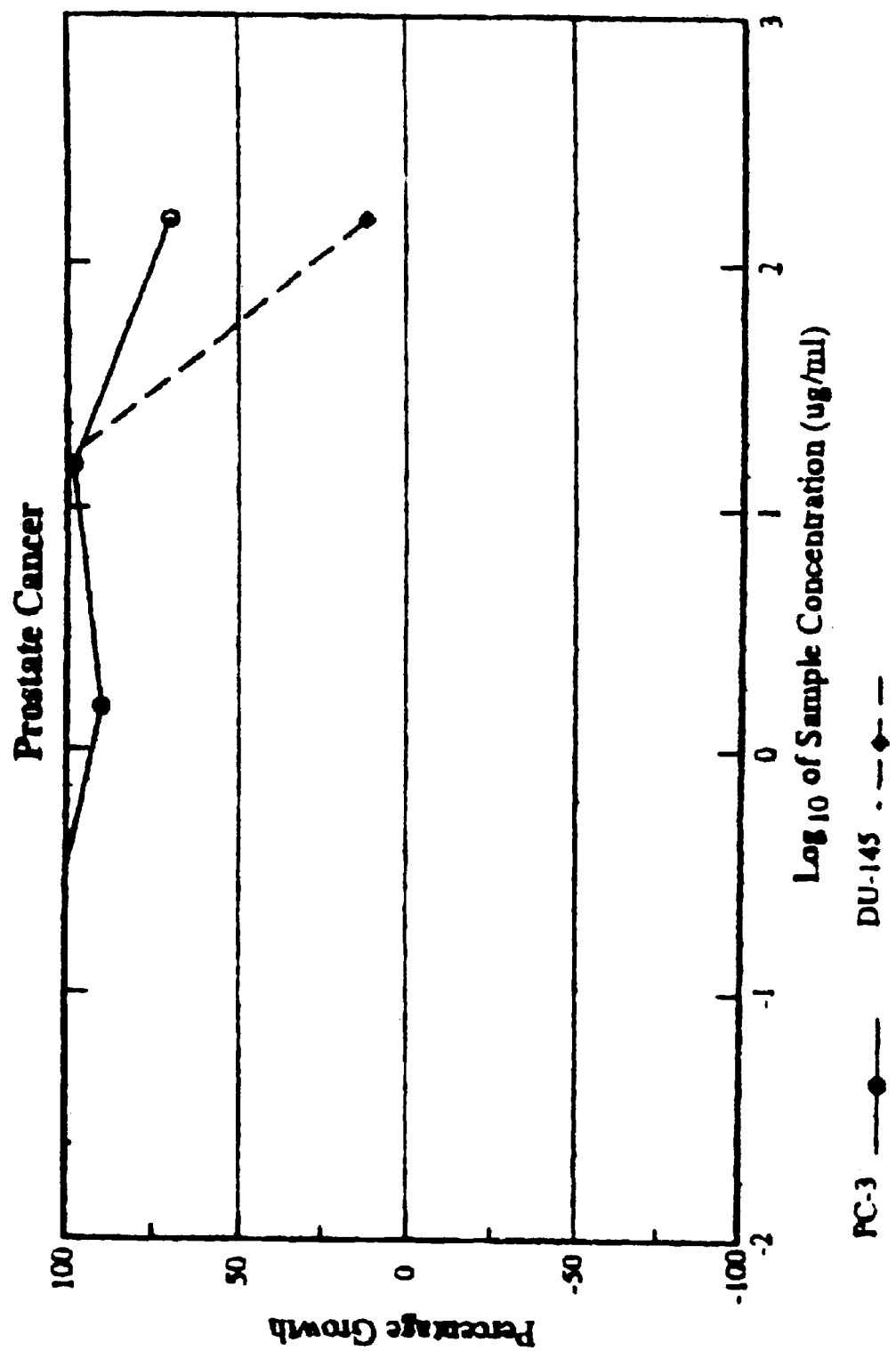
FIG. 5 illustrates the effect of exemplary enzymatic compositions on the growth rate of various prostate cancer cell lines over a 48 hour period when presented at dilutions representing 0.013, 0.13, 1.30, 13, and 130 USP units of papain enzymatic activity per ml of cell culture medium. These enzymatic activities correspond to sample papain/urea cream concentrations of −1.8, −0.8, 0.2, 1.2 and 2.2 ug/ml.
Figure 6:
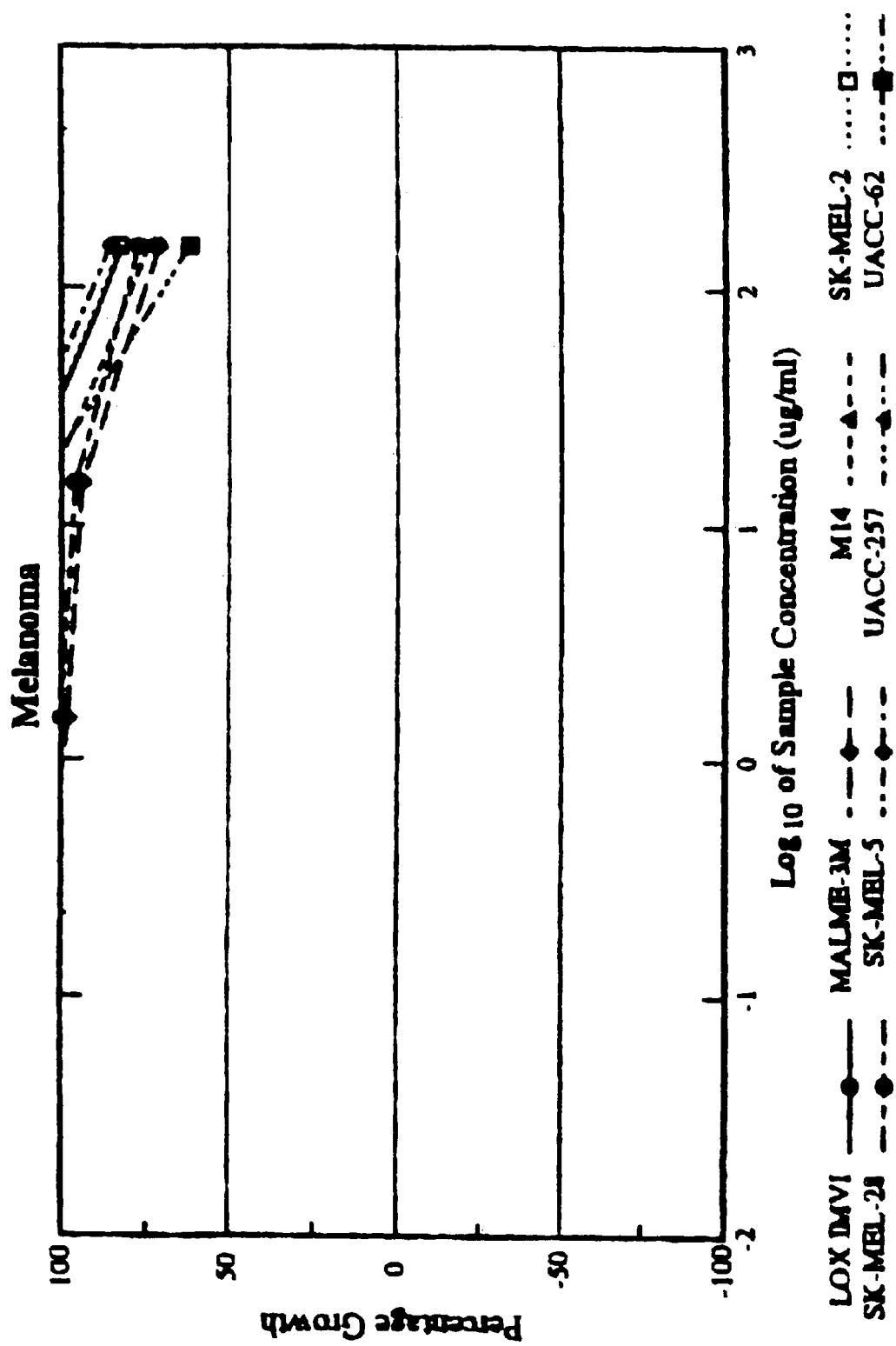
FIG. 6 illustrates the effect of exemplary enzymatic compositions on the growth rate of various melanoma cell lines over a 48 hour period when presented at dilutions representing 0.013, 0.13, 1.30, 13, and 130 USP units of papain enzymatic activity per ml of cell culture medium. These enzymatic activities correspond to sample papain/urea cream concentrations of −1.8, −0.8, 0.2, 1.2 and 2.2 ug/ml.
Figure 7:
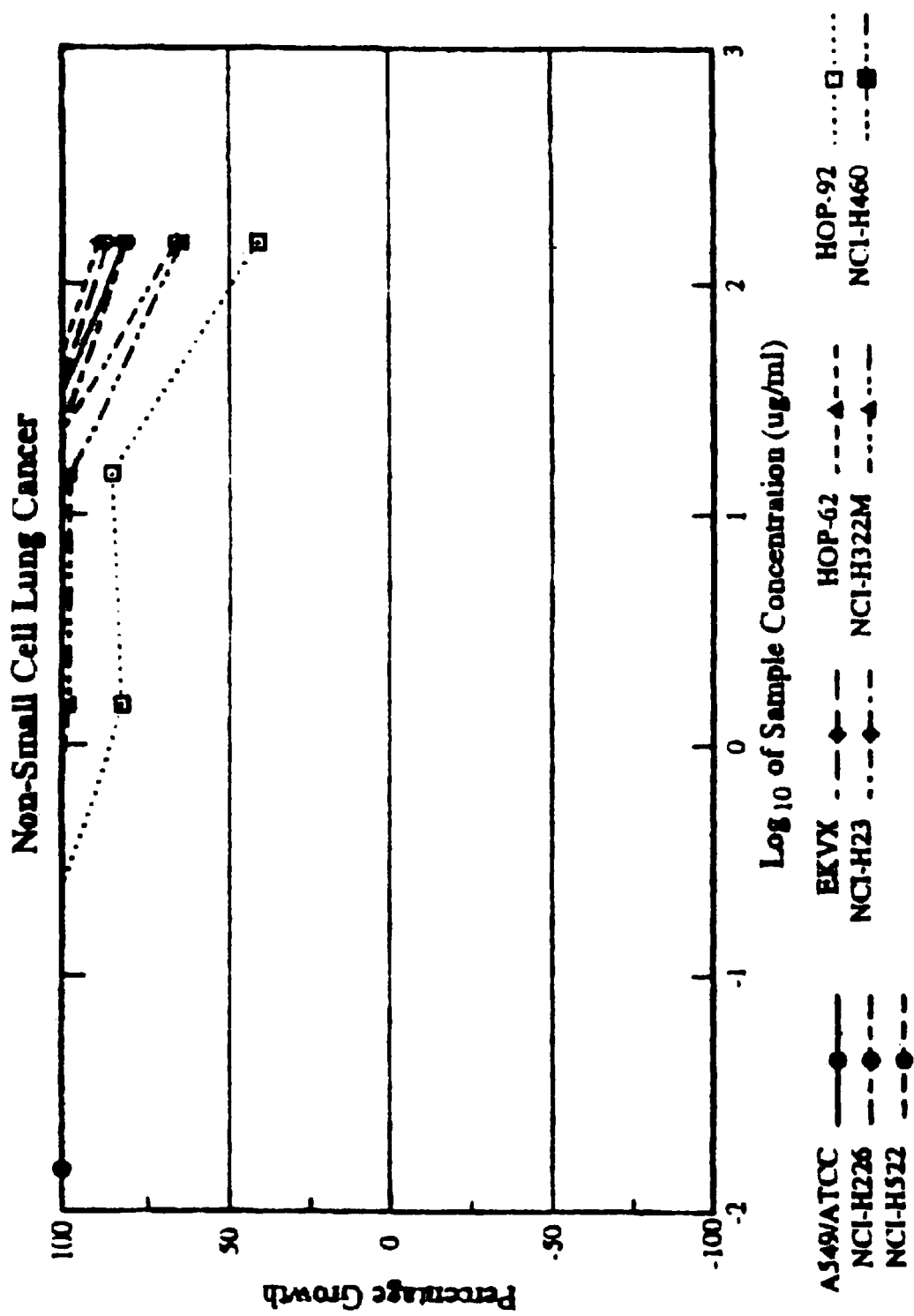
FIG. 7 illustrates the effect of exemplary enzymatic compositions on the growth rate of various non-small cell lung cancer cell lines over a 48 hour period when presented at dilutions representing 0.013, 0.13, 1.30, 13, and 130 USP units of papain enzymatic activity per ml of cell culture medium. These enzymatic activities correspond to sample concentrations of −1.8, −0.8, 0.2, 1.2 and 2.2 ug/ml.
Figure 8:
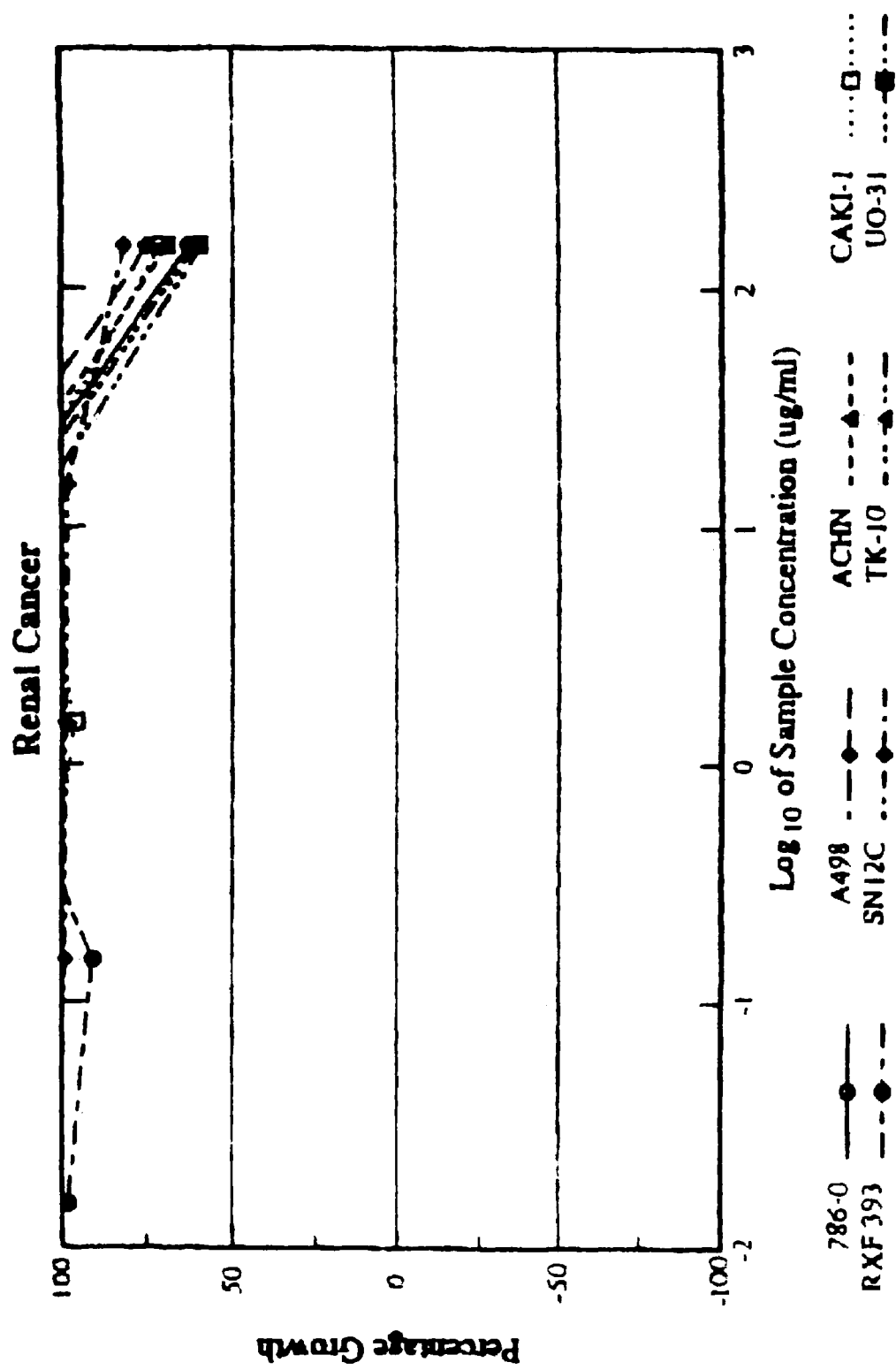
FIG. 8 illustrates the effect of exemplary enzymatic compositions on the growth rate of various renal cancer cell lines over a 48 hour period when presented at dilutions representing 0.013, 0.13, 1.30, 13, and 130 USP units of papain enzymatic activity per ml of cell culture medium. These enzymatic activities correspond to sample papain/urea cream concentrations of −1.8, −0.8, 0.2, 1.2 and 2.2 ug/ml.
Figure 9:
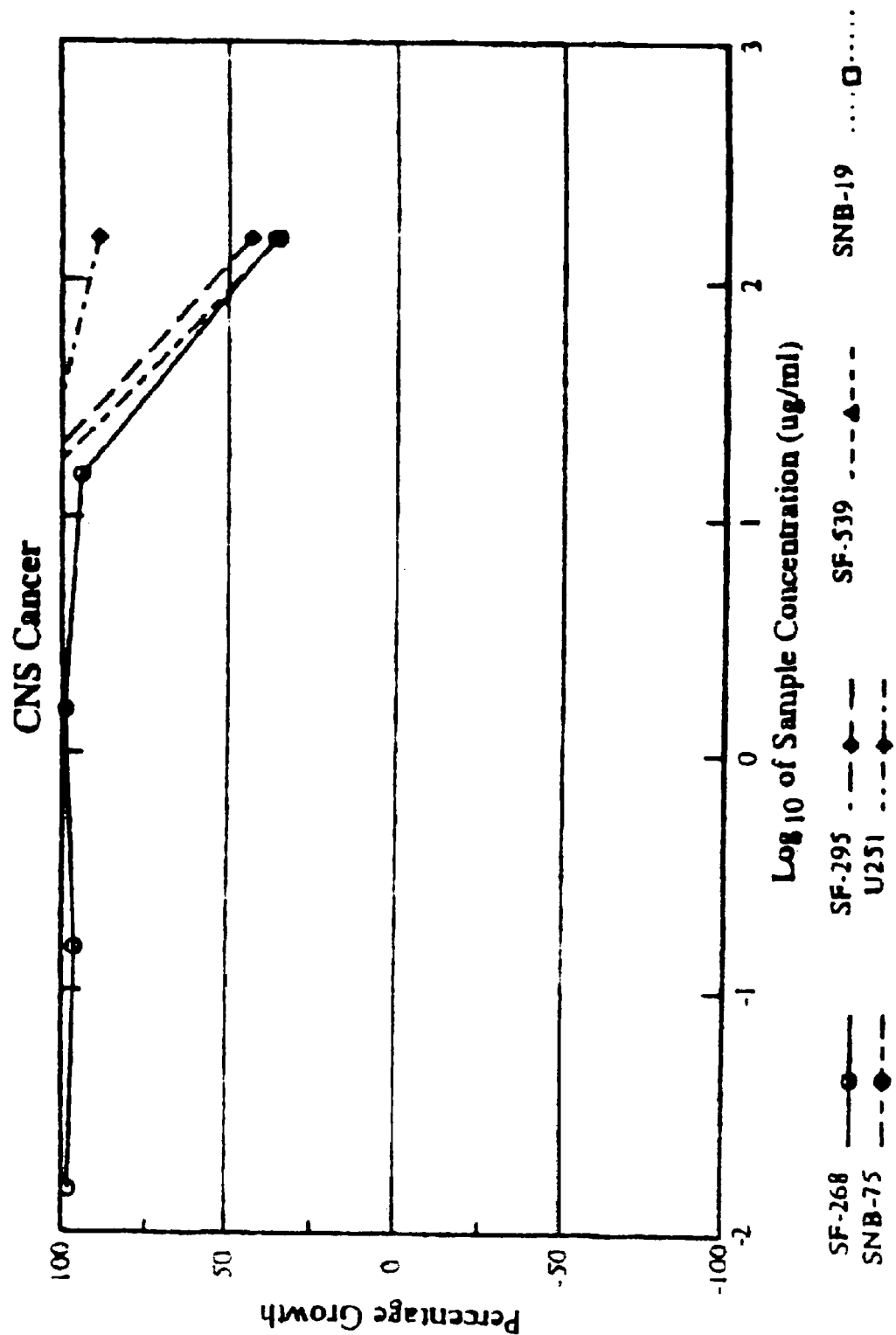
FIG. 9 illustrates the effect of exemplary enzymatic compositions on the growth rate of various central nervous system cancer cell lines over a 48 hour period when presented at dilutions representing 0.013, 0.13, 1.30, 13, and 130 USP units of papain enzymatic activity per ml of cell culture medium. These enzymatic activities correspond to sample papain/urea cream concentrations of −1.8, −0.8, 0.2, 1.2 and 2.2 ug/ml.

As shown in the table below and illustrated in FIGS. 1-9, for many of the cell lines tested significant inhibition of cancer cell growth was observed at the upper end of this concentration range, the threshold dose for a response being between 10 and 100 µgram of ACCUZYME® formulation per milliliter of cell growth solution. At the concentration of 100 µgram/ml, in three quarters of the cell lines—including representatives of each of the 9 cancer types tested—the growth percentage was reduced by at least 10%; in ten of the cell lines the growth was reduced by about 50% or more; and the breast cancer cell line MDA-MB-31/ATCC manifested a 27% negative growth rate, with a calculated GI50 of 43.6 microgram of the ACCUZYME® formulation per ml of the culture medium, or about 36.2 units USP of enzymatic activity per ml of culture medium. By contrast, commercial formulations of the enzyme for topical application are over 20,000-fold more concentrated, for example having 830,000 units USP or more of enzymatic activity per ml of topical medium.

Table of Cancer Cell Line Growth Inhibition as a Function of the Concentration of Debridement Enzyme Cream (micrograms/ml)

| Panel/Cell Line | Time Zero | Control | $Log_{10}$ Concentration | | | | | | | | | | GI50 | TGI | LC50 |
|---|---|---|---|---|---|---|---|---|---|---|---|---|---|---|---|
| | | | -1.8 | -0.8 | 0.2 | 1.2 | 2.2 | -1.8 | -0.8 | 0.2 | 1.2 | 2.2 | | | |
| | | | Mean Optical Densities | | | | | Percent Growth | | | | | | | |
| Leukemia | | | | | | | | | | | | | | | |
| CCRP-CEM | 0.369 | 1.742 | 1.824 | 1.874 | 1.879 | 1.880 | 0.743 | 106 | 110 | 110 | 110 | 27 | 7.97E+01 | >1.60E+02 | >1.60E+02 |
| HL-60 (TB) | 0.295 | 1.467 | 1.499 | 1.598 | 1.510 | 1.426 | 1.469 | 103 | 111 | 104 | 97 | 100 | >1.50E+02 | >1.50E+02 | >1.50E+02 |
| K-562 | 0.101 | 0.733 | 0.693 | 0.763 | 0.727 | 0.731 | 0.228 | 94 | 105 | 99 | 100 | 20 | 6.31E+01 | >1.50E+02 | >1.50E+02 |
| MOLT-4 | 0.508 | 1.768 | 1.928 | 2.059 | 1.928 | 1.788 | 1.391 | 113 | 123 | 113 | 102 | 70 | >1.50E+02 | >1.50E+02 | >1.50E+02 |
| RPMI-8226 | 0.844 | 2.638 | 2.721 | 2.771 | 2.783 | 2.794 | 2.302 | 105 | 107 | 108 | 109 | 81 | >1.50E+02 | >1.50E+02 | >1.50E+02 |
| SR | 0.471 | 1.536 | 1.490 | 1.577 | 1.735 | 1.646 | 0.962 | 96 | 104 | 119 | 110 | 46 | 1.30E+02 | >1.50E+02 | >1.50E+02 |

-continued

Table of Cancer Cell Line Growth Inhibition as a Function of the Concentration of Debridement Enzyme Cream (micrograms/ml)

| Panel/Cell Line | Time Zero | Control | $\log_{10}$ Concentration | | | | | | | | | | GI50 | TGI | LC50 |
|---|---|---|---|---|---|---|---|---|---|---|---|---|---|---|---|
| | | | −1.8 | −0.8 | 0.2 | 1.2 | 2.2 | −1.8 | −0.8 | 0.2 | 1.2 | 2.2 | | | |
| | | | Mean Optical Densities | | | | | Percent Growth | | | | | | | |
| NSC Lung Cancer | | | | | | | | | | | | | | | |
| A549/ATCC | 0.187 | 0.987 | 0.994 | 1.020 | 1.018 | 1.065 | 0.842 | 101 | 104 | 104 | 110 | 82 | >1.50E+02 | >1.50E+02 | >1.50E+02 |
| EKVX | 0.492 | 1.229 | 1.309 | 1.316 | 1.300 | 1.292 | 1.136 | 111 | 112 | 110 | 109 | 87 | >1.50E+02 | >1.50E+02 | >1.50E+02 |
| HOP-62 | 0.716 | 1.415 | 1.431 | 1.508 | 1.504 | 1.492 | 1.345 | 102 | 113 | 113 | 111 | 90 | >1.50E+02 | >1.50E+02 | >1.50E+02 |
| HOP-92 | 0.551 | 0.828 | 0.856 | 0.838 | 0.782 | 0.788 | 0.666 | 110 | 104 | 83 | 86 | 41 | 9.58E+01 | >1.50E+02 | >1.50E+02 |
| NCI-H226 | 0.562 | 1.235 | 1.303 | 1.357 | 1.331 | 1.270 | 1.106 | 110 | 118 | 114 | 105 | 81 | >1.50E+02 | >1.50E+02 | >1.50E+02 |
| NCI-H23 | 0.417 | 1.220 | 1.281 | 1.295 | 1.300 | 1.316 | 1.240 | 108 | 109 | 110 | 112 | 102 | >1.50E+02 | >1.50E+02 | >1.50E+02 |
| NCI-R322M | 0.704 | 1.558 | 1.617 | 1.605 | 1.544 | 1.543 | 1.250 | 107 | 105 | 98 | 98 | 64 | >1.50E+02 | >1.50E+02 | >1.50E+02 |
| NCI-H460 | 0.220 | 1.590 | 1.740 | 1.681 | 1.689 | 1.734 | 1.656 | 111 | 107 | 107 | 111 | 105 | >1.50E+02 | >1.50E+02 | >1.50E+02 |
| NCI-H522 | 0.701 | 1.617 | 1.615 | 1.702 | 1.686 | 1.694 | 1.305 | 100 | 109 | 108 | 108 | 66 | >1.50E+02 | >1.50E+02 | >1.50E+02 |
| Colon Cancer | | | | | | | | | | | | | | | |
| COLO 205 | 0.582 | 1.082 | 1.108 | 1.176 | 1.129 | 1.164 | 1.117 | 105 | 119 | 109 | 116 | 107 | >1.50E+02 | >1.50E+02 | >1.50E+02 |
| HCC 2998 | 0.446 | 1.020 | 1.111 | 1.202 | 1.076 | 1.179 | 1.076 | 116 | 132 | 110 | 128 | 110 | >1.50E+02 | >1.50E+02 | >1.50E+02 |
| HCT-116 | 0.342 | 2.320 | 2.421 | 2.464 | 2.408 | 2.451 | 2.176 | 105 | 107 | 104 | 107 | 93 | >1.50E+02 | >1.50E+02 | >1.50E+02 |
| HCT-15 | 0.251 | 1.614 | 1.727 | 1.737 | 1.716 | 1.721 | 0.953 | 108 | 109 | 107 | 108 | 51 | >1.50E+02 | >1.50E+02 | >1.50E+02 |
| HT-29 | 0.163 | 1.222 | 1.178 | 1.254 | 1.212 | 1.180 | 0.485 | 96 | 103 | 99 | 96 | 30 | 7.54E+01 | >1.50E+02 | >1.50E+02 |
| KM12 | 0.684 | 2.137 | 2.211 | 2.285 | 2.207 | 2.294 | 1.537 | 105 | 110 | 105 | 111 | 59 | >1.50E+02 | >1.50E+02 | >1.50E+02 |
| SW-620 | 0.475 | 2.679 | 2.761 | 2.871 | 2.756 | 2.825 | 2.526 | 104 | 109 | 103 | 107 | 93 | >1.50E+02 | >1.50E+02 | >1.50E+02 |
| CNS Cancer | | | | | | | | | | | | | | | |
| SF-268 | 0.306 | 0.951 | 0.938 | 0.924 | 0.947 | 0.910 | 0.541 | 98 | 96 | 99 | 94 | 36 | 8.70E+01 | >1.50E+02 | >1.50E+02 |
| SF-295 | 0.579 | 1.784 | 1.851 | 1.936 | 1.791 | 1.876 | 1.101 | 106 | 113 | 101 | 108 | 43 | 1.18E+02 | >1.50E+02 | >1.50E+02 |
| SF-539 | 0.495 | 1.492 | 1.577 | 1.577 | 1.588 | 1.623 | 1.506 | 109 | 109 | 110 | 113 | 101 | >1.50E+02 | >1.50E+02 | >1.50E+02 |
| SNB-19 | 0.279 | 1.170 | 1.181 | 1.234 | 1.205 | 1.180 | 1.183 | 101 | 107 | 104 | 101 | 101 | >1.50E+02 | >1.50E+02 | >1.50E+02 |
| RNB-7S | 0.751 | 1.135 | 1.182 | 1.197 | 1.164 | 1.152 | 0.885 | 112 | 116 | 107 | 104 | 35 | 9.07E+01 | >1.50E+02 | >1.50E+02 |
| U251 | 0.241 | 1.278 | 1.343 | 1.387 | 1.353 | 1.330 | 1.161 | 106 | 110 | 107 | 105 | 89 | >1.50E+02 | >1.50E+02 | >1.50E+02 |
| Melanoma | | | | | | | | | | | | | | | |
| LOX IMVI | 0.251 | 2.172 | 2.256 | 2.383 | 2.307 | 2.356 | 1.828 | 104 | 111 | 107 | 110 | 82 | >1.50E+02 | >1.50E+02 | >1.50E+02 |
| MALME-3M | 0.660 | 1.271 | 1.322 | 1.305 | 1.256 | 1.233 | 1.093 | 108 | 106 | 98 | 94 | 71 | >1.50E+02 | >1.50E+02 | >1.50E+02 |
| M14 | 0.340 | 1.362 | 1.394 | 1.406 | 1.391 | 1.395 | 1.094 | 103 | 104 | 103 | 103 | 74 | >1.50E+02 | >1.50E+02 | >1.50E+02 |
| SK-MEL-2 | 0.640 | 1.465 | 1.526 | 1.566 | 1.519 | 1.550 | 1.327 | 107 | 112 | 107 | 110 | 83 | >1.50E+02 | >1.50E+02 | >1.50E+02 |
| SK-MEL-28 | 0.427 | 1.507 | 1.549 | 1.583 | 1.506 | 1.465 | 1.259 | 104 | 107 | 100 | 96 | 77 | >1.50E+02 | >1.50E+02 | >1.50E+02 |
| SK-MEL-5 | 0.623 | 1.945 | 2.078 | 2.158 | 2.043 | 2.129 | 1.761 | 110 | 116 | 107 | 114 | 86 | >1.50E+02 | >1.50E+02 | >1.50E+02 |
| UACC-257 | 0.396 | 0.995 | 1.047 | 1.044 | 1.048 | 1.099 | 1.190 | 109 | 108 | 109 | 117 | 133 | >1.50E+02 | >1.50E+02 | >1.50E+02 |
| UACC-62 | 0.656 | 2.405 | 2.628 | 2.599 | 2.565 | 2.512 | 1.737 | 113 | 111 | 109 | 106 | 62 | >1.50E+02 | >1.50E+02 | >1.50E+02 |
| Ovarian Cancer | | | | | | | | | | | | | | | |
| IGROV1 | 0.397 | 1.131 | 1.046 | 1.070 | 1.102 | 1.071 | 0.924 | 88 | 92 | 96 | 92 | 72 | >1.50E+02 | >1.50E+02 | >1.50E+02 |
| OVCAR-3 | 0.492 | 1.244 | 1.172 | 1.174 | 1.209 | 1.217 | 0.888 | 90 | 91 | 95 | 96 | 53 | >1.50E+02 | >1.50E+02 | >1.50E+02 |
| OVCAR-4 | 0.508 | 1.101 | 1.177 | 1.174 | 1.173 | 1.168 | 0.890 | 113 | 112 | 112 | 111 | 64 | >1.50E+02 | >1.50E+02 | >1.50E+02 |
| OVCAR-5 | 0.357 | 0.946 | 0.984 | 1.004 | 1.022 | 1.052 | 1.007 | 107 | 110 | 113 | 118 | 110 | >1.50E+02 | >1.50E+02 | >1.50E+02 |
| OVCAR-8 | 0.565 | 2.420 | 2.533 | 2.526 | 2.555 | 2.612 | 2.467 | 106 | 106 | 107 | 110 | 103 | >1.50E+02 | >1.50E+02 | >1.50E+02 |
| SK-OV-3 | 0.446 | 1.432 | 1.486 | 1.538 | 1.520 | 1.554 | 1.187 | 105 | 111 | 109 | 112 | 75 | >1.50E+02 | >1.50E+02 | >1.50E+02 |
| Renal Cancer | | | | | | | | | | | | | | | |
| 786 0 | 0.274 | 1.508 | 1.555 | 1.587 | 1.553 | 1.647 | 1.089 | 104 | 107 | 104 | 112 | 63 | >1.50E+02 | >1.50E+02 | >1.50E+02 |
| A498 | 1.120 | 1.650 | 1.752 | 1.782 | 1.723 | 1.761 | 1.519 | 119 | 125 | 114 | 121 | 75 | >1.50E+02 | >1.50E+02 | >1.50E+02 |
| ACHN | 0.362 | 1.491 | 1.612 | 1.671 | 1.695 | 1.665 | 1.142 | 111 | 116 | 118 | 115 | 69 | >1.50E+02 | >1.50E+02 | >1.50E+02 |
| CAKI-1 | 0.822 | 1.351 | 1.421 | 1.376 | 1.331 | 1.404 | 1.200 | 113 | 105 | 96 | 110 | 71 | >1.50E+02 | >1.50E+02 | >1.50E+02 |
| RXF 393 | 0.425 | 0.788 | 0.782 | 0.756 | 0.868 | 0.966 | 0.838 | 98 | 91 | 119 | 149 | 114 | >1.50E+02 | >1.50E+02 | >1.50E+02 |
| SN12C | 0.631 | 2.100 | 2.122 | 2.087 | 2.079 | 2.073 | 1.830 | 102 | 99 | 99 | 98 | 82 | >1.50E+02 | >1.50E+02 | >1.50E+02 |
| TK-10 | 0.584 | 1.137 | 1.194 | 1.205 | 1.176 | 1.153 | 0.910 | 110 | 112 | 107 | 103 | 59 | >1.50E+02 | >1.50E+02 | >1.50E+02 |
| UO-31 | 0.713 | 1.368 | 1.480 | 1.478 | 1.440 | 1.429 | 1.114 | 117 | 117 | 111 | 109 | 61 | >1.50E+02 | >1.50E+02 | >1.50E+02 |
| Prostate Cancer | | | | | | | | | | | | | | | |
| PC-3 | 0.698 | 2.413 | 2.515 | 2.500 | 2.238 | 2.374 | 1.895 | 106 | 105 | 90 | 98 | 70 | >1.50E+02 | >1.50E+02 | >1.50E+02 |
| DE-145 | 0.225 | 0.859 | 0.900 | 0.886 | 0.877 | 0.873 | 0.299 | 106 | 104 | 103 | 102 | 12 | 5.65E+01 | >1.50E+02 | >1.50E+02 |
| Breast Cancer | | | | | | | | | | | | | | | |
| MCP7 | 0.193 | 0.884 | 0.857 | 0.858 | 0.863 | 0.892 | 0.767 | 96 | 96 | 97 | 101 | 83 | >1.50E+02 | >1.50E+02 | >1.50E+02 |
| NCI/ADR-RES | 0.362 | 1.281 | 1.354 | 1.377 | 1.353 | 1.400 | 1.342 | 108 | 110 | 108 | 113 | 107 | >1.50E+02 | >1.50E+02 | >1.50E+02 |
| MDA-MB-231 | 0.544 | 1.272 | 1.464 | 1.378 | 1.369 | 1.393 | 0.396 | 126 | 114 | 113 | 117 | −27 | 4.36E+01 | 9.70E+01 | >1.50E+02 |
| H8 578T | 0.673 | 1.217 | 1.296 | 1.337 | 1.293 | 1.282 | 1.019 | 114 | 122 | 114 | 112 | 64 | >1.50E+02 | >1.50E+02 | >1.50E+02 |
| MDA-MB-435 | 0.523 | 2.046 | 2.154 | 2.138 | 2.076 | 2.170 | 1.817 | 107 | 106 | 102 | 108 | 85 | >1.50E+02 | >1.50E+02 | >1.50E+02 |
| BT-549 | 0.621 | 1.627 | 1.621 | 1.690 | 1.671 | 1.686 | 1.584 | 99 | 106 | 104 | 106 | 96 | >1.50E+02 | >1.50E+02 | >1.50E+02 |
| T-47D | 0.517 | 1.189 | 1.244 | 1.291 | 1.230 | 1.264 | 0.912 | 108 | 115 | 106 | 111 | 59 | >1.50E+02 | >1.50E+02 | >1.50E+02 |

What is claimed is:

1. A method of treating a cancer in a patient, comprising administering to a patient in need thereof a treatment effective amount of a composition consisting of one or more debridement enzymes and one or more denaturants, and a pharmaceutically acceptable carrier, wherein the cancer is a leukemia, ovarian, breast, colon, prostate, lung, renal, or CNS cancer.

2. The method of claim 1 wherein the debridement enzyme is selected from the group consisting of a plasma enzyme, a pancreatic enzyme, a cysteine protease, a serine protease, and a metallopeptidase.

3. The method of claim 1 wherein the debridement enzyme is selected from the group consisting of fibrinolysin, desoxyribonuclease, trypsin, chymotrypsin, krillase, bromelain, papain, ficin, subtilisins, proteinase K, collagenase, vibriolysin, thermolysin, streptokinase and streptodornase.

4. The method of claim 1 wherein the debridement enzyme is papain.

5. The method of claim 1 comprising administering the debridement enzyme in a dose in the range about $1 \times 10^4$ to $1 \times 10^8$ USP per gram.

6. The method of claim 1 comprising administering the debridement enzyme in a dose of about $1.1 \times 10^6$ USP per gram.

7. The method of claim 1 wherein the denaturant is selected from the group consisting of urea, lactic acid, citric acid, an aliphatic alcohol, β-mercaptoethanol, a detergent, sodium dodecyl sulfate, formaldehyde, acetone, acetonitrile, dimethylsulfoxide, dimethylformamide, propylene carbonate, ethylene carbonate, a metal scavenger, crown ethers, a crown amine, a polyether, polyethyleneoxide, a polyamine, polyethyleneamine, cryptands, ethylenediaminetetraacetic acid or its salts, silver sulfadiazine, gentamicin, penicillin, a strong acid, hydrochloric acid, phosphoric acid, sulfuric acid, an acid with a $pK_a$ less than about 4, a strong base, sodium hydroxide, potassium hydroxide, sodium carbonate, and a base with a $pK_a$ greater than about 10.

8. The method of claim 1 wherein the denaturant is urea.

9. The method of claim 4 wherein the denaturant is urea.

10. The method of claim 1 wherein the denaturant is present in concentration range of about 0.1-40 weight percent.

11. The method of claim 1 wherein the denaturant is present in concentration range of about 10 weight percent to 50 weight percent.

12. The method of claim 1 wherein the denaturant is present in concentration range of about 5 weight percent to 20 weight percent.

13. The method of claim 1 wherein the denaturant is present in concentration range of about 1-5 weight percent.

14. The method of claim 1, wherein the enzyme retains at least 80% activity in the presence of the denaturant.

15. The method of claim 1, wherein the enzyme retains at least 90% activity in the presence of the denaturant.

16. The method of claim 1, wherein the enzyme retains at least 95% in the presence of the denaturant.

* * * * *